(12) United States Patent
Li et al.

(10) Patent No.: US 11,715,199 B2
(45) Date of Patent: Aug. 1, 2023

(54) SYSTEMS AND METHODS FOR SURGICAL SMOKE MANAGEMENT

(71) Applicant: Stryker Corporation, Kalamazoo, MI (US)

(72) Inventors: Wenjing Li, Sunnyvale, CA (US); Kundan Krishna, Surrey (CA); Amit A. Mahadik, San Jose, CA (US); Hannes Rau, Milpitas, CA (US)

(73) Assignee: Stryker Corporation, Kalamazoo, MI (US)

( * ) Notice: Subject to any disclaimer, the term of this patent is extended or adjusted under 35 U.S.C. 154(b) by 266 days.

(21) Appl. No.: 17/139,589

(22) Filed: Dec. 31, 2020

(65) Prior Publication Data
US 2021/0202063 A1    Jul. 1, 2021

Related U.S. Application Data

(60) Provisional application No. 62/956,017, filed on Dec. 31, 2019.

(51) Int. Cl.
*A61B 17/00* (2006.01)
*A61B 18/00* (2006.01)
(Continued)

(52) U.S. Cl.
CPC ............ *G06T 7/0012* (2013.01); *A61B 18/00* (2013.01); *A61B 90/36* (2016.02); *G06T 3/40* (2013.01);
(Continued)

(58) Field of Classification Search
None
See application file for complete search history.

(56) References Cited

U.S. PATENT DOCUMENTS

| 7,207,977 B2 | 4/2007 | Thompson et al. |
| 7,245,315 B2 | 7/2007 | Sadok et al. |

(Continued)

FOREIGN PATENT DOCUMENTS

| CN | 108399359 A | 8/2018 |
| EP | 3321858 A1 | 5/2018 |

OTHER PUBLICATIONS

Wang et al., "Asmoke removal method for laparoscopic images," arXiv:1803.08410v1 [cs.CV] Mar. 22, 2018 (Year: 2018).*

(Continued)

*Primary Examiner* — Soo Shin
(74) *Attorney, Agent, or Firm* — Morrison & Foerster LLP

(57) ABSTRACT

Systems and methods for detecting, characterizing, and addressing surgical smoke are disclosed. In some embodiments, a surgical system receives image data representing an image of a surgical environment and generates sets of values based on the received image. The sets of values may include representations of atmospheric light in the image and representations of contrast values in the image. The system may determine from the sets of values whether predetermined smoke severity criteria are met, and may responsively automatically engage and/or disengage one or more surgical devices, such as a surgical smoke evacuation system and/or an image processing system (e.g., a video enhancement feature) configured to improve quality of smoky surgical images.

49 Claims, 15 Drawing Sheets
(8 of 15 Drawing Sheet(s) Filed in Color)

(51) Int. Cl.

| | |
|---|---|
| *A61B 90/00* | (2016.01) |
| *G06T 3/40* | (2006.01) |
| *G06T 7/00* | (2017.01) |
| *G06T 7/73* | (2017.01) |
| *G06V 10/56* | (2022.01) |
| *G06V 10/60* | (2022.01) |
| *G06V 20/52* | (2022.01) |
| *G16H 20/40* | (2018.01) |
| *G16H 30/00* | (2018.01) |

(52) U.S. Cl.
CPC ............... *G06T 7/74* (2017.01); *G06V 10/56* (2022.01); *G06V 10/60* (2022.01); *G06V 20/52* (2022.01); *G16H 20/40* (2018.01); *G16H 30/00* (2018.01); *A61B 2018/00595* (2013.01); *A61B 2018/00982* (2013.01); *G06T 2207/10024* (2013.01); *G06T 2207/30004* (2013.01)

(56) References Cited

U.S. PATENT DOCUMENTS

| | | | |
|---|---|---|---|
| 7,280,696 | B2 | 10/2007 | Zakrzewski et al. |
| 7,609,856 | B2 | 10/2009 | Chen et al. |
| 8,009,932 | B2 | 8/2011 | Zhou et al. |
| 8,497,898 | B2 | 7/2013 | Moriyama et al. |
| 9,255,907 | B2 | 2/2016 | Heanue et al. |
| 9,609,852 | B2 | 4/2017 | Cote |
| 9,805,472 | B2 | 10/2017 | Chou et al. |
| 10,395,498 | B2 | 8/2019 | Mills et al. |
| 10,706,544 | B2 | 7/2020 | Hiltl et al. |
| 2009/0123074 | A1 | 5/2009 | Chen et al. |
| 2016/0239967 | A1* | 8/2016 | Chou ............... G06T 7/254 |
| 2016/0247276 | A1* | 8/2016 | Chou ............... G06V 10/755 |
| 2018/0271615 | A1* | 9/2018 | Mahadik ........... A61K 49/0017 |

OTHER PUBLICATIONS

Chen et al., "De-smokeGCN: Generative Cooperative Networks for Joint Surgical Smoke Detection and Removal," IEEE Transactions on Medical Imaging, vol. 39, No. 5, May 2020 (Year: 2020).*

Bertalmio et al. "Navier-Stokes, Fluid Dynamics, and Image and Video Inpainting," Proceedings of the 2001 Computer Society Conference on Computer Vision and Pattern Recognition, Dec. 8-14, 2001, Kauai, HI, USA; pp. 1-9.

International Preliminary Report on Patentability dated Jul. 5, 2022, directed to International Application No. PCT/US2020/067678; 17 pages.

International Search Report and Written Opinion dated Mar. 29, 2021, directed to International Application No. PCT/US2020/067678; 23 pages.

Jiang et al., (Jul. 2017) "Fog Density Estimation and Image Defogging Based on Surrogate Modeling for Optical Depth," IEEE Transactions on Image Processing 26(7): 3397-3409.

Lee et al., "Fog Degree Measurement based on Local Contrast and Color Similarity," 2017 14th International Conference on Ubiquitous Robots and Ambient Intelligence (URAI), Jun. 28-Jul. 1, 2017, Jeju, Korea; pp. 517-519.

Leibetseder et al. "Real-Time Image-based Smoke Detection in Endoscopic Videos," Thematic Workshops '17, Oct. 23-27, 2017, Mountain View, California, USA; pp. 296-304.

Queiroz et al. "Automatic Segmentation of Specular Reflections for Endoscopic Images Based on Sparse and Low-Rank Decomposition," 2014 27th SIBGRAPI Conference on Graphics, Patterns and Images, Aug. 26-30, 2014, Brazil; 282-289.

Tchaka et al. (2017). "Chromaticity Based Smoke Removal in Endoscopic Images," Medical Imaging 2017: Image Processing 10133; 8 pages.

Yeh et al. (Nov. 1, 2013). "Haze effect removal from image via haze density estimation in optical model," Optics Express 21(22): 27127-27141.

Loukas et al. (2015). "Smoke detection in endoscopic surgery videos: a first step towards retrieval of semantic events," The International Journal of Medical Robotics and computer Assisted Surgery 11:80-94.

* cited by examiner

SYSTEMS AND METHODS FOR SURGICAL SMOKE MANAGEMENT

CROSS-REFERENCE TO RELATED APPLICATIONS

This application claims the priority of U.S. Provisional Application No. 62/956,017, filed Dec. 31, 2019, the entire contents of which are incorporated herein by reference.

FIELD

The present disclosure relates generally to surgical procedures, and more specifically systems and methods for surgical smoke management.

BACKGROUND

Surgical smoke is the gaseous by-product produced during surgical procedures. Generally, surgical smoke is produced by, for example, electrocautery devices, laser ablation, ultrasound scalpels, high speed drills, burrs, and/or saws, due to disruption and vaporization of tissue protein and fat. Electro-cauterization is a surgical procedure in which a surgeon uses electricity to heat tissue in order to prevent or stop bleeding, remove abnormal tissue, and/or prevent infection. Electro-cauterization may generate surgical smoke. Surgical smoke may hinder the vision of the surgeon, produce an unpleasant odor and release harmful substances into the air. To ensure safety of medical staff and patients, and to optimize the efficiency and efficacy of surgical procedures, proper management of surgical smoke, including detection and characterization during surgery is important. Existing techniques for management of surgical smoke may depend on manual decisions made by surgeons and/or nurses in the operating room, and may depend on manual activation or deactivation of surgical equipment for addressing surgical smoke.

SUMMARY

According to an aspect, a smoke management system disclosed herein may be configured to receive medical or surgical images and/or video and to analyze one or more frames of the received image data in order to efficiently and accurately detect the presence of surgical smoke and characterize a level of surgical smokiness. Surgical smoke assessment may be performed by modeling surgical smoke as haze in outdoor scene images, estimating smoke severity based on attenuation along a line of sight due to atmospheric absorption and scattering. Specifically, optionally, the image analysis techniques disclosed herein may be configured to generate, based on a received image frame, a representation of atmospheric light of the image frame and a representation of a contrast of the image frame. Based on the atmospheric light and the contrast, the system may perform one or more linear regressions, upon which one or more exponential calculations generating a smoke severity indicator (e.g., score) may be based. Optionally, the system may characterize a severity of surgical smoke in the input image frame, for example by comparing the smoke severity indicator to one or more predetermined threshold values. Optionally, in accordance with the determined severity of surgical smoke, the system may automatically engage and/or disengage one or more surgical devices, such as a surgical smoke evacuation system and/or an image processing system (e.g., a video enhancement feature) configured to improve quality of smoky surgical images.

According to an aspect, a smoke management system disclosed herein may be configured to receive medical or surgical images and/or video and to analyze one or more frames of the received image data in order to efficiently and accurately detect a spark generated from a tip of a cauterization tool. Recognition of a cauterization spark in image data may be accomplished using a specular reflection algorithm. Detection of specular regions in a consecutive number of frames may be used to identify when the endoscope has entered and/or is within the surgical ambience (ie. when the endoscope has entered and/or is within the subject) as opposed to being located external to the subject, and the system may use said identification to trigger automatic engagement and/or disengagement of one or more surgical devices or methods for smoke management.

Recognition of a cauterization spark in image data may serve as an indication of a cauterization event, and the system may use said indication to trigger automatic engagement and/or disengagement of one or more surgical devices.

Use of the systems, methods, and techniques described herein during surgical procedures (e.g., endoscopic, other minimally invasive, or non-invasive surgical procedures) may allow surgeons to have an optimal visual endoscopic video and to focus on the surgical procedure without the distraction of manually assessing, characterizing, or addressing optical smoke. Furthermore, the systems described herein can also optimize the usage of the smoke evacuation systems, conserving gas and decreasing the likelihood that a gas tank may need to be changed during a surgical procedure.

According to an aspect, a first surgical system is provided, the system comprising: one or more processors configured to: receive image data representing an image of a surgical environment; generate, based on the received image data, a set of one or more values representing atmospheric light of the image data; generate, based on the received image data, a set of one or more representative contrast values; determine, based on the one or more values representing atmospheric light and based on the one or more representative contrast values, whether the received image data satisfies one or more surgical smoke conditions.

Optionally, the set of one or more values representing atmospheric light of the image data is generated by the system based on a set of one or more values representing a bright channel of the image data. The set of one or more values representing the bright channel may be generated by the system based on the image data.

Optionally, generating the set of one or more values representing the bright channel of the image data comprises: for each pixel of the image data, selecting, as a respective bright channel pixel value, a maximum color-channel value from among a group of pixels of the image data within a respective patch including the respective pixel.

Optionally, generating the set of one or more values representing atmospheric light comprises: calculating a first term comprising a set of one or more maximum values of the one or more values representing the bright channel; calculating a second term comprising a set of one or more representative bright-channel values based on the one or more values representing the bright channel; calculating a sum of the first term and the second term to generate the set of one or more values representing atmospheric light.

Optionally, calculating the first term comprises generating a one-dimensional matrix based on the one or more values representing the bright channel.

Optionally, calculating the second term comprises generating a one-dimensional matrix based on the one or more values representing the bright channel.

Optionally, the first term is weighted by a constant $c_1$.

Optionally, the second term is weighted by a second constant equal to $(1-c_1)$.

Optionally, the set of one or more representative contrast values is generated by the system based on the one or more values representing the bright channel of the image data and based on one or more values representing a dark channel of the image data; and the set of one or more values representing the dark channel is generated by the system based on the image data.

Optionally, generating the set of one or more values representing the dark channel of the image data comprises: for each pixel of the image data, selecting, as a respective dark channel pixel value, a minimum color-channel value from among a group of pixels of the image data within a respective patch including the respective pixel.

Optionally, generating the set of one or more representative contrast values comprises: calculating a third term comprising a set of one or more representative bright-channel values based on the one or more values representing the bright channel; calculating a fourth term comprising a set of one or more representative dark-channel values based on the one or more values representing the dark channel; calculating a set of one or more difference values based on a difference between the fourth term and the third term to generate the set of one or more representative contrast values.

Optionally, determining whether the received image data satisfies one or more surgical smoke conditions comprises calculating a smoke degree score based on the set of one or more values representing atmospheric light of the image data and based on the set of one or more representative contrast values.

Optionally, calculating the smoke degree score comprises performing one or more linear regressions based on the set of one or more values representing atmospheric light of the image data and based on the set of one or more representative contrast values.

Optionally, calculating the smoke degree score comprises calculating an exponential value based on one or more slopes of the one or more linear regressions.

Optionally, the exponential value is calculated based on an exponent comprising a term based on a sum of two or more of the slope values.

Optionally, determining whether the received image data satisfies one or more surgical smoke conditions comprises comparing the smoke degree score to a first threshold value.

Optionally, determining whether the received image data satisfies one or more surgical smoke conditions comprises calculating an adjusted set of one or more atmospheric light values.

Optionally, determining whether the received image data satisfies one or more surgical smoke conditions comprises: comparing the adjusted set of one or more values representing atmospheric light of the image data to a second threshold value; and comparing the set of one or more representative contrast values to a third threshold value.

Optionally, the system further comprises a surgical device configured to automatically change between activation states, wherein the processor is further configured to: based on the determination of whether the received image data satisfies the one or more surgical smoke conditions, automatically change an activation state of the surgical device.

Optionally, changing the activation state of the surgical device comprises performing an operation selected from turning the device on and turning the device off.

Optionally, the surgical device comprises a smoke evacuation system.

Optionally, the surgical device comprises an image processing system.

Optionally, the image data representing the image of a surgical environment is a region extracted from an image larger than the region.

Optionally, the one or more processors are configured to perform a scaling operation on the image data.

According to an aspect, a first method, performed at a surgical system, is provided, the method comprising: receiving image data representing an image of a surgical environment; generating, based on the received image data, a set of one or more values representing atmospheric light of the image data; generating, based on the received image data, a set of one or more representative contrast values; determining, based on the one or more values representing atmospheric light and based on the one or more representative contrast values, whether the received image data satisfies one or more surgical smoke conditions.

According to an aspect, a first non-transitory computer-readable storage medium is provided, the on-transitory computer-readable storage medium storing instructions configured to be executed by a surgical system and to cause the surgical system to: receive image data representing an image of a surgical environment; generate, based on the received image data, a set of one or more values representing atmospheric light of the image data; generate, based on the received image data, a set of one or more representative contrast values; determine, based on the one or more values representing atmospheric light and based on the one or more representative contrast values, whether the received image data satisfies one or more surgical smoke conditions.

According to an aspect, a second surgical system is provided, the system comprising: one or more processors configured to: receive image data representing an image of a surgical environment; detect, based on the received image data, one or more saturated regions in the image; detect, based on the received image data, one or more high-intensity regions in the image data; generate, based on the one or more saturated regions and on the one or more high-intensity regions, data representing cauterization light sparks in the image Optionally, detecting the one or more saturated regions in the image data is based on red channel data of the image data.

Optionally, detecting the one or more saturated regions in the image data comprises applying an adaptive threshold to the image data.

Optionally, detecting the one or more high-intensity regions in the image data is based on green channel data of the image data.

Optionally, detecting the one or more high-intensity regions in the image data comprises applying open top-hat with reconstruction filters to the image data.

Optionally, the reconstruction filters comprise different sizes of structuring elements and different corresponding thresholds.

Optionally, generating the data representing cauterization light sparks in the image comprises modeling cauterization light sparks in the image data as one or more of the high-intensity regions surrounded by one or more of the saturated regions.

Optionally, the data representing cauterization light sparks in the image comprises a mask.

Optionally, the second system further comprises a surgical device configured to automatically change between activation states, wherein the processor is further configured to: based on the data representing cauterization light sparks in the image, automatically determine whether to change an activation state of the surgical device.

Optionally, automatically determining whether to change the activation state of the surgical device comprises comparing the data representing cauterization light sparks to one or more threshold values.

Optionally, changing the activation state of the surgical device comprises performing an operation selected from turning the device on and turning the device off.

Optionally, the surgical device comprises a smoke evacuation system.

Optionally, the surgical device comprises an image processing system.

Optionally, the image data representing the image of a surgical environment is a region extracted from an image larger than the region.

Optionally, the one or more processors are configured to perform a scaling operation on the image data.

Optionally, the one or more processors configured to generate, based on the one or more saturated regions and on the one or more high-intensity regions, data representing one or more specular reflection regions in the image.

Optionally, generating the data representing one or more specular reflection regions comprises generating a combined mask based on the one or more saturated regions and on the one or more high-intensity regions Optionally, the one or more processors are configured to generate modified image data by compensating the one or more specular reflection regions.

Optionally, compensating the one or more specular reflection regions comprises applying one or more inpainting techniques to compensate the one or more specular reflection regions based on neighborhood information.

According to an aspect, a second method is provided, the method performed at a surgical system, the method comprising: receiving image data representing an image of a surgical environment; detecting, based on the received image data, one or more saturated regions in the image; detecting, based on the received image data, one or more high-intensity regions in the image data; generating, based on the one or more saturated regions and on the one or more high-intensity regions, data representing cauterization light sparks in the image.

According to an aspect, a second non-transitory computer-readable storage medium is provided, the storage medium storing instructions configured to be executed by a surgical system and to cause the surgical system to: receive image data representing an image of a surgical environment; detect, based on the received image data, one or more saturated regions in the image; detect, based on the received image data, one or more high-intensity regions in the image data; generate, based on the one or more saturated regions and on the one or more high-intensity regions, data representing cauterization light sparks in the image.

According to an aspect, a third surgical system is provided, the system comprising: one or more processors configured to: receive image data representing an image of a surgical environment; generate, based on the received image data, a set of one or more values representing atmospheric light of the image data; generate, based on the received image data, a set of one or more representative contrast values; determine, based on the one or more values representing atmospheric light and based on the one or more representative contrast values, whether the received image data satisfies one or more surgical smoke conditions; detect, based on the received image data, one or more saturated regions in the image; detect, based on the received image data, one or more high-intensity regions in the image data; generate, based on the one or more saturated regions and on the one or more high-intensity regions, data representing cauterization light sparks in the image.

Optionally, the third system further comprises a surgical device configured to automatically change between activation states, wherein the processor is further configured to: based on the determination of whether the received image data satisfies the one or more surgical smoke conditions and based on the data representing cauterization light sparks in the image, automatically determine whether to change an activation state of the surgical device.

According to an aspect, a third method is provided, the method performed at a surgical system, the method comprising: receiving image data representing an image of a surgical environment; generating, based on the received image data, a set of one or more values representing atmospheric light of the image data; generating, based on the received image data, a set of one or more representative contrast values; determining, based on the one or more values representing atmospheric light and based on the one or more representative contrast values, whether the received image data satisfies one or more surgical smoke conditions; detecting, based on the received image data, one or more saturated regions in the image; detecting, based on the received image data, one or more high-intensity regions in the image data; generating, based on the one or more saturated regions and on the one or more high-intensity regions, data representing cauterization light sparks in the image.

According to an aspect, a third non-transitory computer-readable storage medium is provided, the storage medium storing instructions configured to be executed by a surgical system and to cause the surgical system to: receive image data representing an image of a surgical environment; generate, based on the received image data, a set of one or more values representing atmospheric light of the image data; generate, based on the received image data, a set of one or more representative contrast values; determine, based on the one or more values representing atmospheric light and based on the one or more representative contrast values, whether the received image data satisfies one or more surgical smoke conditions; detect, based on the received image data, one or more saturated regions in the image; detect, based on the received image data, one or more high-intensity regions in the image data; generate, based on the one or more saturated regions and on the one or more high-intensity regions, data representing cauterization light sparks in the image.

It will be appreciated that any of the aspects, features and options described in view of the system apply equally to the method and computer-readable storage medium, and vice versa. It will also be clear that any one or more of the above aspects, features and options can be combined. According to an aspect, any one or more of the characteristics of any one or more of the systems, methods, and/or computer-readable storage mediums recited above may be combined, in whole or in part, with one another and/or with any other features or characteristics described elsewhere herein.

BRIEF DESCRIPTION OF THE DRAWINGS

The patent or application file contains at least one drawing executed in color. Copies of this patent or patent application publication with color drawings(s) will be provided by the Office upon request and payment of the necessary fee. Features will become apparent to those of ordinary skill in the art by describing in detail exemplary embodiments with reference to the attached drawings in which:

FIG. 3A shows a high-smoke image, FIG. 3B shows a medium-smoke image, and FIG. 3C shows a low-smoke image.

FIG. 4A shows a low-smoke image and FIG. 4B shows a high-smoke image.

DETAILED DESCRIPTION

Reference will now be made in detail to implementations and embodiments of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Figure 1:
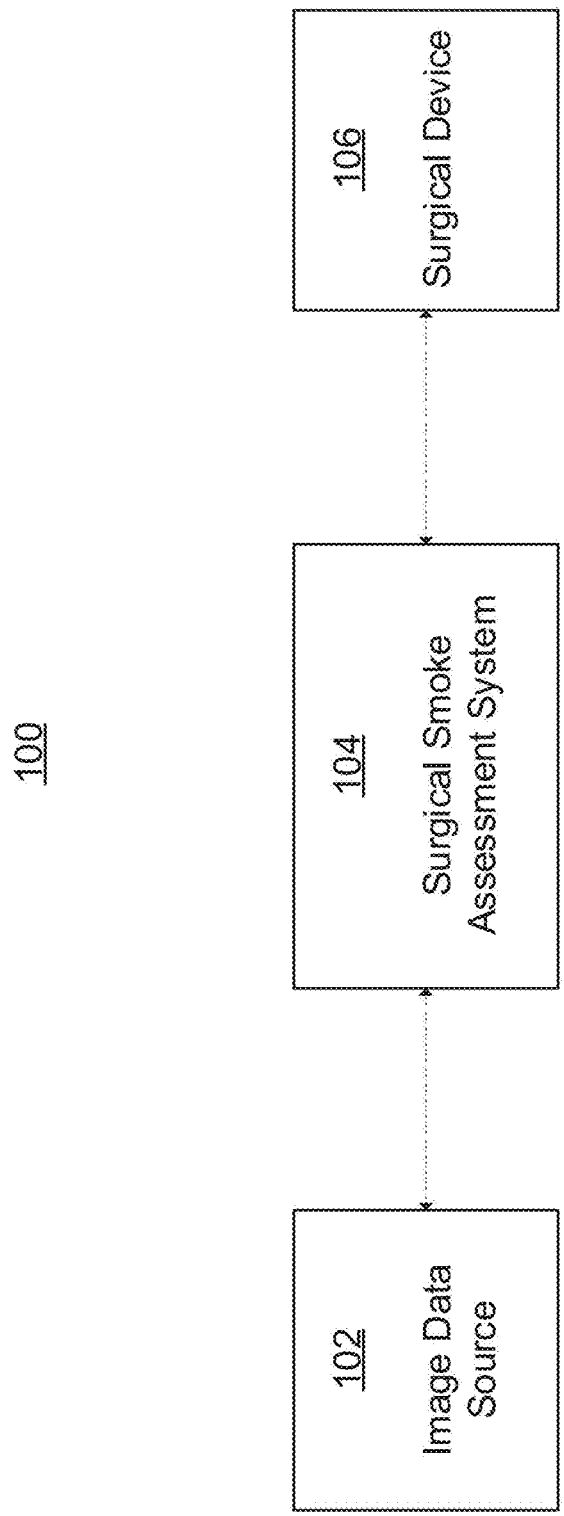
FIG. 1 depicts a system for managing surgical smoke, in accordance with some embodiments.

FIG. 1 depicts a system 100 for managing surgical smoke, in accordance with some embodiments.

As shown, system 100 may include image data source 102, surgical smoke assessment system 104, and surgical device 106. Each of these components may be communicatively coupled with one another such that they may send and receive electronic information via network communication amongst one another. As shown in the example of FIG. 1, assessment system 104 may be communicatively coupled to both image data source 102 and to surgical system 106.

In some embodiments, image data source 102 may be any electronic source for medical or surgical images and/or video, such as an image capture device, an image-capture and/or video-capture endoscope, an image or video broadcasting or relaying device, one or more servers, and/or one or more databases or repositories. Image data source 102 may be configured to transmit image data (e.g., medical/surgical image data and/or medical/surgical video data) to surgical smoke assessment system 104 by any wired or wireless electronic communication medium, including by any suitable network communication protocol.

In some embodiments, surgical smoke assessment system 104 may be any device or system comprising one or more computer processors configured to receive image data, assess and/or process the received image data, and to generate and transmit one or more output signals in accordance with the results of the image assessment. In some embodiments, assessment system 104 may be provided, in whole or in part, as all or part of a desktop computing device, laptop, tablet, mobile electronic device, dedicated medical image processing device, computing module, processor, server, cloud computing system, distributed computing system, or the like. In some embodiments, surgical smoke assessment system 104 may be provided locally with respect to surgical device 106 (e.g., in the surgical suite), while in some embodiments surgical smoke assessment system 104 may be provided remotely from surgical device 106 (e.g., outside the surgical suite, elsewhere in a hospital, at a remote server location, etc.).

In some embodiments, assessment system 104 may be configured to receive image data (e.g., image and/or video data showing a surgical image) from image data source 102 and to process the image to determine a level (e.g., severity) of surgical smoke depicted in the image data received. In some embodiments, assessment system 104 may be configured to determine a level of surgical smoke in accordance with the techniques discussed below with reference to FIGS. 2A-2B.

In some embodiments, assessment system 104 may be configured to send one or more instruction or control signals to surgical device 106 configured to cause surgical device to alter an activation state of the device (e.g., to turn from off to on, or to turn from on to off); in some embodiments, as discussed in detail herein, the instruction or control signal may be sent by assessment system 104 in accordance with the determined level of surgical smoke based on analysis of the image data received. For example, in some embodiments, if the level exceeds a predetermined threshold, then a signal may be sent directing surgical device 106 to be turned on; in some embodiments, if the level falls below a predetermined threshold, then a signal may be sent directing surgical device 106 to be turned off.

In some embodiments, surgical device 106 may be any surgical device, medical device, imaging device, or the like, that is configured to be activated and/or deactivated (or to otherwise have an activation state set or changed) in accordance with an instruction received from surgical smoke assessment system 104. In some embodiments, surgical device 106 may be wholly hardware, wholly software, or may comprise both hardware and software. In some embodiments, surgical device 106 may be a physical device, such as a smoke evacuation system configured to physically remove surgical smoke from a surgical environment. In some embodiments, surgical device 106 may be a software component, such as image processing software configured to process one or more medical images (including, for example, the medical image received from image data source 102 and analyzed to determine a smoke level to determine whether to activate and/or deactivate device 106) to improve image quality for smoky images.

As described herein, surgical device 106 may be configured to be turned on or off in accordance with a smoke level, as determined by system 104. Thus, for example, in the case where device 106 is a smoke mitigation device or performs a smoke mitigation or management function, then device 106 may be turned on when smoke levels are determined to be higher and/or turned off when smoke levels are determined to be lower.

As discussed above, in some embodiments, device 106 may be configured to have an activation state modified in accordance with an instruction signal or control signal received from surgical smoke assessment system 104. In some embodiments, device 106 may be configured to receive instruction signals and/or control signals from surgical smoke assessment system 104 by any wired or wireless electronic communication medium, including by any suitable network communication protocol.

FIG. 2 depicts a flowchart representing an exemplary method 200 for managing surgical smoke, in accordance with some embodiments. As described below in detail, method 200 may enable a surgical smoke management system to receive surgical images or videos, to process the surgical images or videos to determine a level of surgical smoke shown in the image or video, and to automatically disable or disable one or more surgical smoke management devices based on the determined level of surgical smoke.

In some embodiments, method 200 may be carried out, in whole or in part, by one or more of the components of a system for managing surgical smoke, such as system 100 described above with respect to FIG. 1. In some embodiments, any one or more of the aspects of method 200 may be combined, in whole or in part, with any one or more of the aspects of FIG. 1, and/or with any one or more of the systems, methods, devices, and/or techniques described elsewhere herein.

At block 202, in some embodiments, the system may receive image data representing an image of a surgical environment. In the example of system 100, surgical smoke assessment system 104 may receive image data representing an image of a surgical environment from image data source 102.

The image data received by the system may be in the form of a still image or one or more frames of a video image, and may depict a surgical environment (e.g., an area in and/or near a tissue segment on which surgery is being performed) with an unknown level of surgical smoke present (including, in some embodiments, no surgical smoke). The image data may be received from an image or video capture device, an image or video broadcasting or relaying device, one or more servers, and/or one or more databases or repositories. The image data received may be received via any suitable form of electronic communication, including wired and/or wireless network communication.

The image data received by the system may comprise a plurality of pixels. One or more of the plurality of pixels constituting the image data may, in some embodiments, be associated with one or more values indicating a brightness (e.g., intensity) for the pixel. In some embodiments, a pixel may be associated with a plurality of values, with each value representing a different color-channel for the pixel. In some embodiments, each pixel may comprise three color-channel values, e.g., one value each for a red, green, and blue color-channel for each pixel.

Figure 2A:
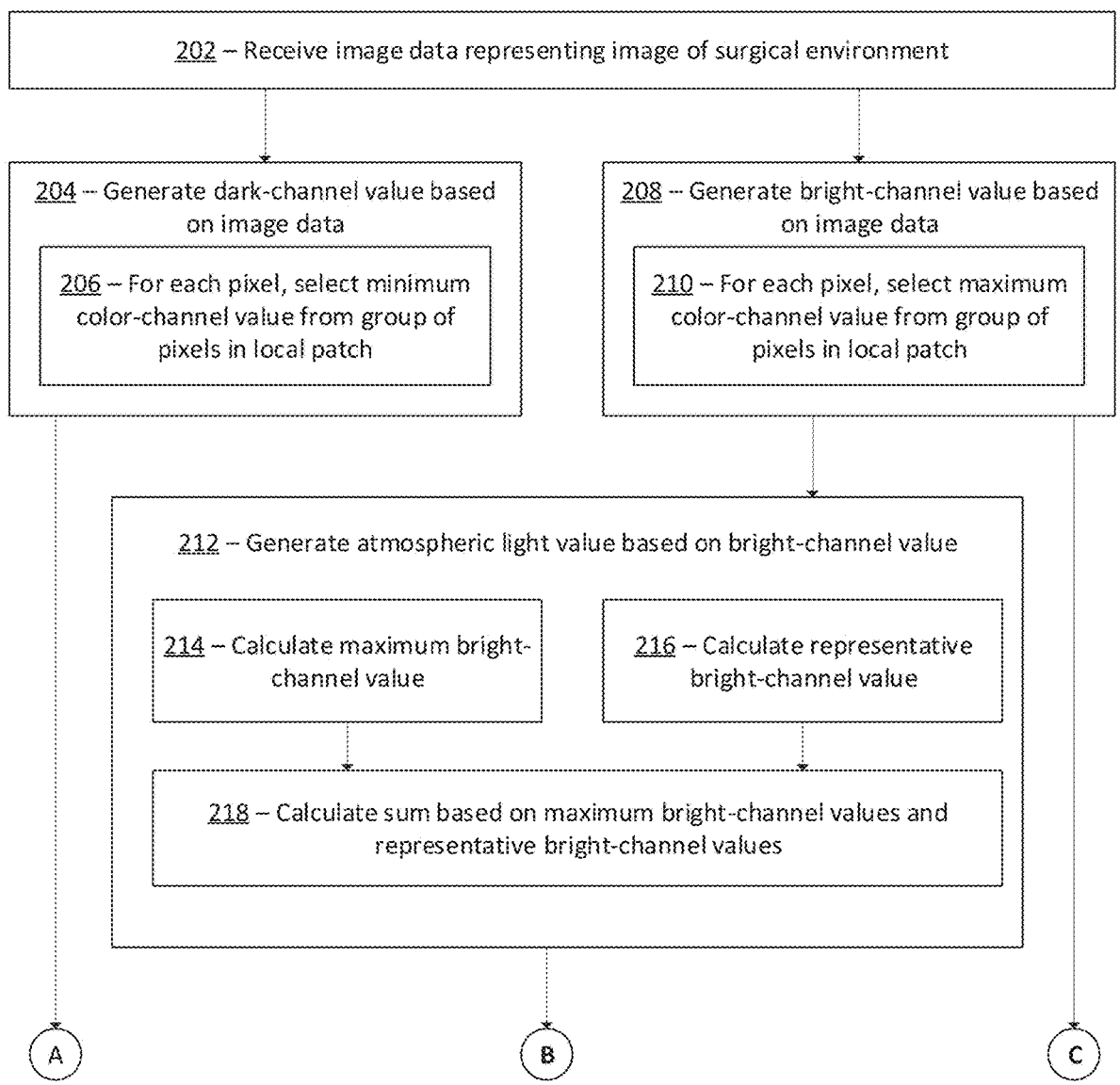
FIGS. 2A-2B depict a flowchart representing an exemplary method for managing surgical smoke, in accordance with some embodiments.
Figure 2B:
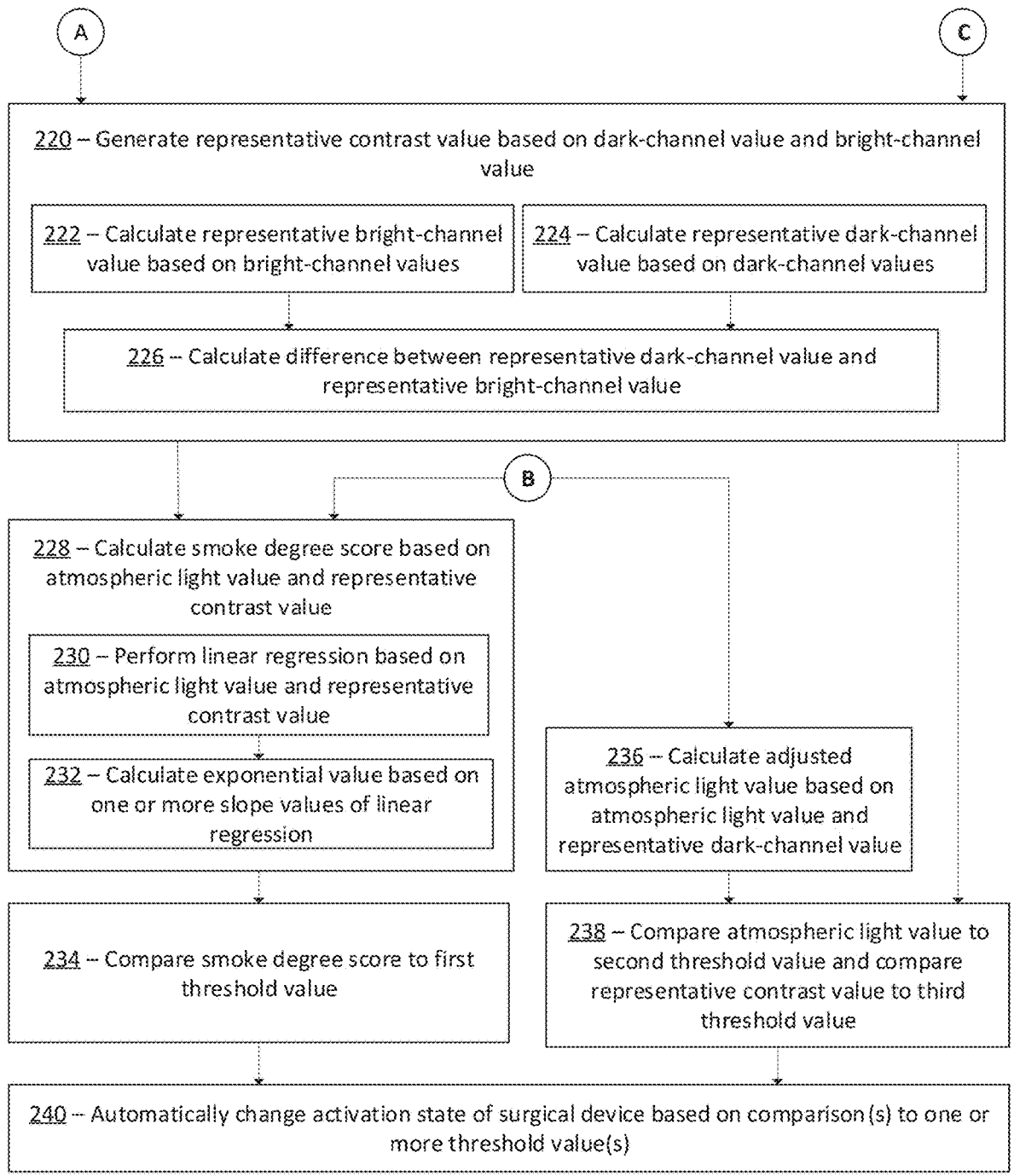

In some embodiments, the system may perform one or more image pre-processing techniques on the received image data (not shown in FIG. 2A). For example, the system may perform cropping, alignment, and/or re-sizing (e.g., scaling) of the received image data before additional processing steps are performed.

In some embodiments, a cropping procedure may comprise identifying a region-of-interest (ROI) in the image data received, such that additional image processing techniques such as those described below may be performed only on the ROI selected, rather than on the entire original image. In some embodiments, an ROI may be selected manually by a user of the system. In some embodiments, an ROI may be selected automatically by one or more algorithms. In some embodiments, an ROI may be selected automatically as a predefined area (e.g., a predefined rectangular area of a given image size, e.g., a given pixel size) within a field of view of the received image data. In some embodiments, an ROI may be selected automatically as a region defined by a finding circle image processing approach, in which intersection points between a scope edge and a diagonal line of an image frame are used as reference points to calculate an inner rectangle defining the ROI.

In some embodiments, an alignment procedure may comprise rotating or aligning all or part of the received image data, such that additional image processing techniques such as those described below may be performed only on the aligned image, rather than on the entire original image.

In some embodiments, a scaling procedure may comprise scaling (e.g., resizing) all or part of the received image data, such that additional image processing techniques such as those described below may be performed only on the scaled image, rather than on the entire original image. For example, an image may be reduced in size such that the reduced-size, downscaled image may be used for one or more of the image processing techniques described below, rather than the original full-size image.

In some embodiments, more than one of the image pre-processing techniques may be performed on the same image data. For example, a single image frame may be subject to any two or more image preprocessing techniques before proceeding to the image processing techniques discussed below. In some embodiments, no image preprocessing techniques may be employed (e.g., the raw image data initially received may be used for the image processing steps described below).

At block 204, in some embodiments, the system may generate one or more dark-channel values based on the received image data. As discussed above, pre-processing techniques may be optionally performed before block 204. Thus, "based on the received image data" may encompass, in some embodiments, processing the received image data without using any pre-processing techniques, as well as, in some other embodiments, processing the received image data after previously applying one or more image pre-processing techniques. The same principle applies to other blocks discussed below with respect to method 200.

In some embodiments, the dark-channel value of block 204 may be generated on a pixel-by-pixel basis for all or part of the received image data (e.g., for the entire ROI of the received image). In some embodiments, for a given pixel, the dark-channel value may be generated with reference to one or more other pixels in the same image (e.g., in the same image frame).

At block 206, in some embodiments, generating the one or more dark-channel values may comprise selecting a minimum color-channel value from a group of pixels in a local patch. For example, for a given pixel, the dark-channel value may be generated with reference to a patch of pixels in the vicinity of the given pixel; e.g., a square or rectangular patch of a predefined size may be defined surrounding the given pixel, and all pixels in that patch may be analyzed in order to determine the dark-channel value for the given pixel. In some embodiments, the local patch may be 5 pixels, 10 pixels, 15 pixels, or 25 pixels in length and/or height. Once the local patch is defined, the system may select the minimum single color-channel value (e.g., the lowest value representing the lowest-intensity color value) from all color channels of all pixels in the patch, and that value may represent the dark-channel value for the given pixel for which the patch was defined. This process may be repeated for each pixel in the image data being processed, with each pixel defining its own local patch and being accordingly assigned its own dark-channel value.

In some embodiments, for an arbitrary frame image J, the dark channel $J^{dark}$ is given by expression (1), where $J^C$ is a color channel of J and $\Omega(x)$ is a local patch centered as x.

$$J^{Dark}(x) = \min_{c \in (r,g,b)} \left( \min_{y \in \Omega(x)} (J^c(y)) \right) \tag{1}$$

where $J^{Dark}$ is a two-dimensional matrix whose height and width are equal to the number of pixels in height and the number of pixels in width, respectively, of the processed portion of the input image frame (e.g., of the ROI of the image being analyzed). Thus, each value in the matrix $J^{Dark}$ may correspond to a respective pixel of the analyzed portion of the image frame, and each value may represent a darkest local color-channel value for the patch associated with the respective pixel.

In some embodiments, based on observation of smoke-free images, for most patches, at least one color channel has some pixels whose intensity is very low and close to zero. In other words, in most patches, the minimum intensity in the patch is close to zero.

At block 208, in some embodiments, the system may generate one or more bright-channel values based on the received image data. In some embodiments, the bright-channel value may be generated on a pixel-by-pixel basis for all or part of the received image data (e.g., for the entire ROI of the received image). In some embodiments, for a given pixel, the bright-channel value may be generated with reference to one or more other pixels in the same image (e.g., in the same image frame).

At block 210, in some embodiments, generating the one or more bright-channel values may comprise selecting a maximum color-channel value from a group of pixels in a local patch. For example, for a given pixel, the bright-channel value may be generated with reference to a patch of pixels in the vicinity of the given pixel; e.g., a square or rectangular patch of a predefined size may be defined surrounding the given pixel, and all pixels in that patch may be analyzed in order to determine the dark-channel value for the given pixel. In some embodiments, the local patch may be 5 pixels, 10 pixels, 15 pixels, or 25 pixels in length and/or height. In some embodiments, the bright-channel value for a pixel may be determined with reference to a same local patch as the local patch used to determine the dark-channel value for the same pixel, as discussed above with reference to blocks 204-206; in some embodiments, different patches may be used to determine a bright-channel value and a dark-channel value for the same pixel.

For the bright-channel value, once the local patch is defined, the system may select the maximum single color-channel value (e.g., the highest value representing the highest-intensity color value) from all color channels of all pixels in the patch, and that value may represent the bright-channel value for the given pixel for which the patch was defined. This process may be repeated for each pixel in the image data being processed, with each pixel defining its own local patch and being accordingly assigned its own bright-channel value.

In some embodiments, for an arbitrary frame image J, the bright channel $J^{Bright}$ is given by expression (2).

$$J^{Bright}(x) = \max_{c \in (r,g,b)} \left( \max_{y \in \Omega(x)} (J^c(y)) \right) \tag{2}$$

where $J^{Bright}$ is a two-dimensional matrix whose height and width are equal to the number of pixels in height and the number of pixels in width, respectively, of the processed portion of the input image frame (e.g., of the ROI of the image being analyzed). Thus, each value in the matrix $J^{Bright}$ may correspond to a respective pixel of the analyzed portion of the image frame, and each value may represent a brightest local color-channel value for the patch associated with the respective pixel.

In some embodiments, based on observation of smoky images, a higher bright-channel image value may be indicative of heavier smoke and/or bright-color objects.

At block 212, in some embodiments, the system may generate one or more atmospheric light values based on the one or more bright-channel values. In some embodiments, the atmospheric light value may be used to estimate ambient surgical light to determine a smoke score, as discussed below. In some embodiments, as described below, atmospheric light may be represented as a vector. In some embodiments, as described below, atmospheric light may be estimated as a vector of a linear combination of a bright-channel vector and a maximum of a bright channel vector.

At block 214, in some embodiments, generating the one or more atmospheric light values may comprise calculating one or more maximum bright-channel values. In some embodiments, calculating a maximum bright-channel value for image data may comprise performing one or more mathematical operations on the bright-channel value(s) determined above at block 208. In some embodiments, calculating a maximum bright-channel value for image data may comprise performing one or more matrix operations on the bright-channel value(s) determined above at block 208. In some embodiments, a matrix operation may be performed on the $J^{Bright}$ matrix discussed above. For example, the maximum value may be given by expression (3)

$$\max(J^{Bright}) \tag{3}$$

where the max(A) operation operates on a two-dimensional matrix A to yield a one-dimensional matrix, where each value in the one-dimensional matrix is a maximum value of a corresponding column or row of the input matrix A. In some embodiments, $\max(J^{Bright})$ may yield a one-dimensional matrix, with each entry in the one-dimensional matrix representing a maximum value of a column of the two-dimensional $J^{Bright}$ matrix.

At block 216, in some embodiments, generating the one or more atmospheric light values may comprise calculating one or more representative bright-channel values. In some embodiments, calculating a representative bright-channel value for image data may comprise performing one or more mathematical operations on the bright-channel value(s) determined above at block 208. In some embodiments, calculating a representative bright-channel value for image data may comprise performing one or more matrix operations on the bright-channel value(s) determined above at block 208. In some embodiments, a matrix operation may be performed on the $J^{Bright}$ matrix discussed above. In some embodiments, the matrix operation may be different from a matrix operation performed to calculate a maximum value as discussed above at block 214. In some embodiments, the representative value may be given by expression (4)

$$\frac{\text{sum}(J^{Bright})}{(m*n)} \qquad (4)$$

where the sum(A) operation operates on a two-dimensional matrix A to yield a one-dimensional matrix, where each value in the one-dimensional matrix is a sum of the values of a corresponding column or row of the input matrix A, and where m and n are a pixel-height and pixel-width of the portion of the image data being analyzed (e.g., m*n is the pixel size of the image frame J). In some embodiments, sum($J^{Bright}$) may yield a one-dimensional matrix, with each entry in the one-dimensional matrix representing a sum of the corresponding column of the two-dimensional $J^{Bright}$ matrix.

At block 218, in some embodiments, generating the one or more atmospheric light values may comprise calculating one or more sums based on the one or more maximum bright-channel values and the one or more representative bright-channel values. In some embodiments, the one or more sums may be based on a sum of a first term and a second term, wherein the first term is based on the one or more maximum bright-channel values and the second term is based on the one or more representative bright-channel values. In some embodiments, one or more of the first term and the second term may be weighted by a respective constant weighting value. In some embodiments, the respective weighting values may sum to 1. In some embodiments, the one or more sums may be given by expression (5)

$$\text{atm\_light} = \max(J^{Bright}) * c_1 + \frac{\text{sum}(J^{Bright})}{(m*n)} * c_2 \qquad (5)$$

where $c_1$ and $c_2$ are the respective constant weighting values. In some embodiments, $c_1$ and $c_2$ may sum to 1. In some embodiments $c_1$ may be equal to ⅓ and $c_2$ may be equal to ⅔. In some embodiments, $c_1$ and $c_2$ may be any set of two nonzero numbers greater than 0 and less than 1 wherein $c_1$ and $c_2$ sum to 1.

At block 220, in some embodiments, the system may generate one or more representative contrast values based on the one or more dark-channel values and the one or more bright-channel values. As explained below, in some embodiments, the representative contrast value may be calculated based on a difference between a representative dark-channel value and a representative bright-channel value.

At block 222, in some embodiments, generating the one or more representative contrast values may comprise calculating one or more representative bright-channel values based on the one or more bright-channel values. In some embodiments, calculating the one or more representative bright-channel values may share any one or more characteristics in common with the techniques discussed above with respect to block 216. In some embodiments, the one or more representative bright-channel values may be the same as the one or more representative bright-channel values calculated at block 216. In some embodiments, the one or more representative bright-channel values may be given by expression (4) shown above.

At block 224, in some embodiments, generating the one or more representative contrast values may comprise calculating one or more representative dark-channel values based on the one or more dark-channel values. In some embodiments, calculating the one or more representative bright-channel values may share any one or more characteristics in common with the techniques discussed above with respect to blocks 216-218, applied to the dark-channel values in place of the bright-channel values.

In some embodiments, calculating a representative dark-channel value for image data may comprise performing one or more mathematical operations on the dark-channel value(s) determined above at block 208. In some embodiments, calculating a representative dark-channel value for image data may comprise performing one or more matrix operations on the dark-channel value(s) determined above at block 204. In some embodiments, a matrix operation may be performed on the $J^{Dark}$ matrix discussed above. In some embodiments, the matrix operation may be different from a matrix operation performed to calculate a maximum value as discussed above at block 214. In some embodiments, the representative value may be given by expression (6)

$$\frac{\text{sum}(J^{Dark})}{(m*n)} \qquad (6)$$

where the sum(A) operation operates on a two-dimensional matrix A to yield a one-dimensional matrix, where each value in the one-dimensional matrix is a sum of the values of a corresponding column or row of the input matrix A, and where m and n are a pixel-height and pixel-width of the portion of the image data being analyzed (e.g., m*n is the pixel size of the image frame J). In some embodiments, sum($J^{Dark}$) may yield a one-dimensional matrix, with each entry in the one-dimensional matrix representing a sum of the corresponding column of the two-dimensional $J^{Dark}$ matrix.

At block 226, in some embodiments, generating the one or more representative contrast values may comprise calculating a difference between the representative dark-channel value and the representative bright-channel value. In some embodiments, the representative dark-channel value and the representative bright-channel value used to calculate the difference may be calculated in the manner discussed above at blocks 222 and 224.

In some embodiments, the one or more representative contrast values may be equal to the difference between the representative dark-channel value and the representative bright channel value. In some embodiments, the one or more representative contrast values may be based on, but not equal to, the difference between the representative dark-channel value and the representative bright channel value. In some embodiments, the one or more representative contrast values may be given by expression (7)

$$\text{contrast} = \left(\frac{\text{sum}(J^{Dark})}{(m*n)} - \frac{\text{sum}(J^{Bright})}{(m*n)}\right) \qquad (7)$$

At blocks 228-238, in some embodiments, the calculated one or more atmospheric light values and the calculated one or more representative contrast values may be used to determine whether to automatically change an activation state of one or more surgical devices. At blocks 228-234, in some embodiments, a calculated smoke degree score may be compared to a first threshold value to determine whether to change an activation state of the one or more surgical devices. At block 236, in some embodiments, a set of one or more adjusted atmospheric light values and the calculated one or more representative contrast values may be compared to respective second and third threshold values to determine whether to change an activation state of the one or more surgical devices.

Attention is first directed to blocks 228-234, at which a calculated smoke degree score may be compared to a first threshold value to determine whether to change an activation state of the one or more surgical devices.

At block 228, in some embodiments, the system calculates a smoke degree score based on the one or more atmospheric light values and based on the one or more representative contrast values. In some embodiments, the one or more atmospheric light values may be the one or more atmospheric light values calculated at blocks 212-218. In some embodiments, the one or more representative contrast values may be the one or more representative contrast values calculated at blocks 220-226.

At block 230, in some embodiments, calculating the smoke degree score may comprise performing one or more linear regressions based on the one or more atmospheric light values and based on the one or more representative contrast values. In some embodiments, the one or more linear regressions may be one or more linear regressions between the one or more atmospheric light values and any other suitable value or set of values based on the one or more representative contrast values (including, in one example, the one or more representative contrast values themselves).

In some embodiments, a first one of the one or more linear regressions may be a linear regression between the one or more representative contrast values and the one or more atmospheric light values; for example, the first one of the one or more linear regressions may be a linear regression between contrast (shown above at expression (7)) and atm_light (shown above at expression (5)). The first one of the one or more linear regressions may have a slope of $X_1$.

In some embodiments, a second one of the one or more linear regressions may be a linear regression between a difference value and the one or more atmospheric light values, wherein the difference value may itself be based on a difference between the one or more representative contrast values and the one or more atmospheric light values. In some embodiments, the difference value may be given by expression (8)

$$\text{diff}=(\text{atm\_light}-\text{contrast}) \qquad (8)$$

such that the second one of the one or more linear regressions may be a linear regression between diff (shown above at expression (8)) and atm_light (shown above at expression (5)). The first one of the one or more linear regressions may have a slope of $X_2$.

At block 234, in some embodiments, calculating the smoke degree score may comprise calculating an exponential value based on one or more slope values of the one or more linear regressions. In some embodiments, the one or more linear regressions may include the one or more linear regressions discussed above at block 230, and the one or more slope values may include $X_1$ and $X_2$.

In some embodiments, the smoke degree score may be given by expression (9)

$$S=\exp(c_3-(c_4*X_2+c_5*X_1)/c_6) \qquad (9)$$

where $c_3$, $c_4$, $c_5$, and $c_6$ are respective constant values.

In some embodiments, $c_3$ may be equal to 0.2461.
In some embodiments, $c_4$ may be equal to 5.1.
In some embodiments, $c_5$ may be equal to 2.9.
In some embodiments, $c_6$ may be equal to 2.

At block 234, in some embodiments, the system may compare the smoke degree score to a first threshold value. In some embodiments, the first threshold value may be experimentally determined, may be automatically determined by the system, may be manually determined by a user, may be predetermined, and/or may be variable in accordance with one or more surgical conditions.

At block 240, in some embodiments, the system may automatically change an activation state of one or more surgical devices based on comparison of the smoke degree score to the first threshold value. In some embodiments, the one or more surgical devices may include any of the one or more surgical devices discussed elsewhere herein, including a smoke evacuation system and/or a medical image processing system configured to digitally process smoky medical images. In the example of system 100, the one or more surgical devices may include surgical device 106. In some embodiments, the surgical device may comprise an indicator device configured to indicate to a human operator that one or more other surgical devices should be activated and/or deactivated.

In some embodiments, changing an activation state may comprise changing a device from inactive (e.g., off) to active (e.g., on) or changing a device from active (e.g., on) to inactive (e.g., off). In some embodiments, the system may be configured such that, if the smoke degree score exceeds the first threshold value, the one or more surgical devices may be automatically activated. In some embodiments, the system may be configured such that, if the smoke degree score does not exceed the first threshold value, the one or more surgical devices may be automatically deactivated.

In some embodiments, activation or deactivation of the one or more surgical devices may be performed on the basis of the comparison of the smoke degree score to the first threshold alone. In some embodiments, activation or deactivation of the one or more surgical devices may be performed on the basis of one or more additional trigger conditions also being satisfied.

Attention is now directed to blocks 236-238, at which a set of one or more adjusted atmospheric light values and the calculated one or more representative contrast values may be compared to respective second and third threshold values to determine whether to change an activation state of the one or more surgical devices.

At block 236, in some embodiments, the system may calculate one or more adjusted atmospheric light values based on the calculated set of one or more atmospheric light values. For example, the one or more atmospheric light values calculated at blocks 220-226 may be adjusted. In some embodiments, the atmospheric light value(s) may be adjusted by weighting the value by a constant (e.g., by multiplying it by a constant). In some embodiments, the atmospheric light value(s) may be adjusted by adding or subtracting one or more values to or from the atmospheric light value(s). In one embodiment, the adjusted atmospheric light value may be given by expression (10)

$$\text{atm\_light\_adj} = \left(\text{atm\_light} - \frac{\text{sum}(J^{Dark})}{(m*n)}\right) \quad (10)$$

such that the adjusted atmospheric light value atm_light_adj is calculated as the difference between the (unadjusted) atmospheric light value atm_light and a set of one or more representative dark-channel values given by expression (6).

At block 238, in some embodiments, the system may compare the one or more adjusted atmospheric light values to a second threshold value and may compare the one or more representative contrast values to a third threshold value. In some embodiments, one or both of the second and third threshold values may be experimentally determined, may be automatically determined by the system, may be manually determined by a user, may be predetermined, and/or may be variable in accordance with one or more surgical conditions.

At block 240, in some embodiments, the system may automatically change an activation state of one or more surgical devices based on comparison of the one or more adjusted atmospheric light values to the second threshold value and/or based on comparison of the one or more representative contrast values to the third threshold value.

As discussed above, in some embodiments, changing an activation state may comprise changing a device from inactive (e.g., off) to active (e.g., on) or changing a device from active (e.g., on) to inactive (e.g., off). In some embodiments, the system may be configured such that a condition must be met with respect to the second threshold value in order for an activation state of the one or more surgical devices to be changed; in some embodiments, the system may be configured such that a condition must be met with respect to the third threshold value in order for an activation state of the one or more surgical devices to be changed; in some embodiments, the system may be configured such that conditions with respect to the first threshold value and the second threshold value must both be met in order for an activation state of the one or more surgical devices to be changed.

In some embodiments, if one or more conditions with respect to the one or more thresholds are satisfied, the one or more surgical devices may be automatically activated. In some embodiments, if one or more conditions with respect to the one or more thresholds are satisfied, the one or more surgical devices may be automatically deactivated.

In some embodiments, activation or deactivation of the one or more surgical devices may be performed on the basis of one or more of the comparisons at block 238 alone. In some embodiments, activation or deactivation of the one or more surgical devices may be performed on the basis of one or more additional trigger conditions also being satisfied. In some embodiments, one or more of the adjusted atmospheric light values and/or one or more of the representative contrast values may be compared to one or more additional threshold values, different from the second and third threshold values, as an additional trigger condition to changing an activation state of the one or more surgical devices.

In some embodiments, activation or deactivation of the one or more surgical devices may be automatically performed on the basis alone of one or more trigger conditions as recited herein being met (e.g., for a single frame). In some embodiments, activation or deactivation of the one or more surgical devices may be performed on the basis of one or more additional trigger conditions also being satisfied. In some embodiments, one or more trigger conditions (including those recited herein) may be required to be met for a certain consecutive number of frames analyzed (e.g., in a surgical video feed) before changing an activation state. In some embodiments, an activation state may be prevented from being changed, despite one or more trigger conditions being met as discussed herein, during a predefined or dynamically determined period of time, such as for a predefined period of time after the activation state was previously changed.

Figure 3A:
FIGS. 3A-3C show a first example set of surgical images with various degrees or levels of smoke, where
Figure 3B:
Figure 3C:

FIGS. 3A-3C show a first example set of surgical images with various degrees of smokiness, where FIG. 3A shows a high-smoke image, FIG. 3B shows a medium-smoke image, and FIG. 3C shows a low-smoke image.

Figure 4A:
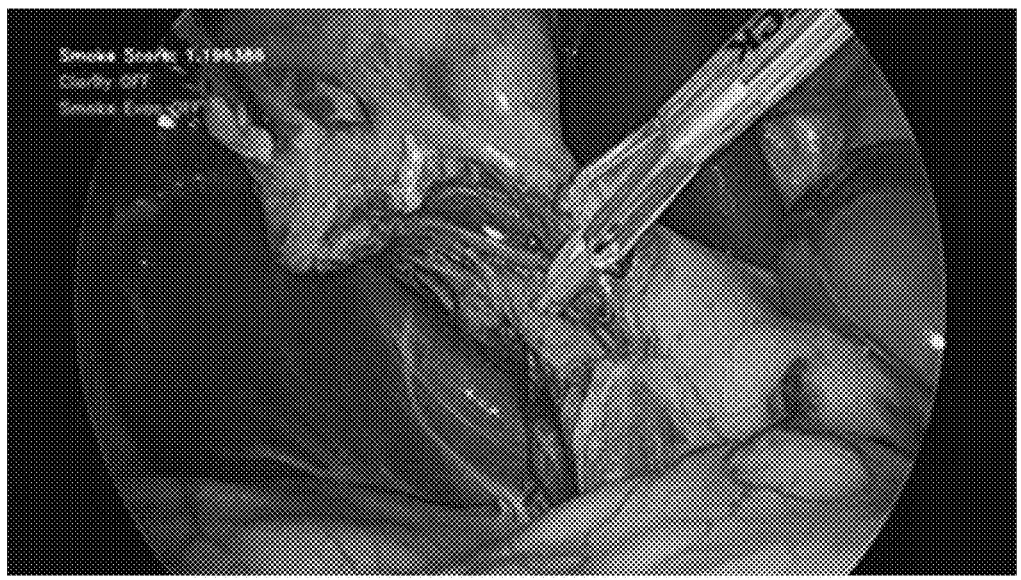
FIGS. 4A-4B show a second example set of surgical images with various degrees or levels of smoke, where
Figure 4B:

FIGS. 4A-4B show a second example set of surgical images with various degrees of smoke, where FIG. 4A shows a low-smoke image and FIG. 4B shows a high-smoke image.

It should be noted that the techniques disclosed herein may be used to characterize image smokiness, e.g., as "no smoke," "low smoke," "medium smoke" "high smoke," "very high smoke," or the like. For example, rather than using a single threshold value to determine whether to activate or deactivate a surgical device (or in addition to doing so), a system may be configured to generate (and store, output, and/or transmit) an indication of one of a plurality of smoke levels (as shown for example in FIGS. 3A-3C and 4A-4B) based on a plurality of thresholds demarcating different smoke levels.

In some embodiments, one or more of the techniques described herein for detecting and/or managing surgical smoke may include (and/or may be applied along with) one or more methods or method steps for image calibration. In some embodiments, during a surgical procedure, different light sources and/or different cameras may be used (e.g., based on different procedure types and/or a clinical user's preference), for example leading to different image brightness.

In some embodiments, one or more techniques may be applied to calibrate images before applications of techniques for characterizing and/or quantifying smokiness (e.g., to standardize a smoke score) across different light sources, different cameras, and/or different camera settings. In some embodiments, an image calibration step may be performed, for example to calibrate an image (e.g., a frame) before using the calibrated image for assessment, characterization, quantification, and/or management of smoke as otherwise disclosed herein.

In some embodiments, a calibration method may include using a calibration factor to calibrate values for an image. In some embodiments, the calibration factor may be calculated based on the uncalibrated image itself. In some embodiments, an intensity calibration method may include the following steps: (1) convert an uncalibrated image from RGB to grayscale; (2) calculate a calibration factor by using a neutral gray value (e.g., 127 for an 8-bit image) divided by an average intensity of the grayscale image; and (3) multiply each of the three RGB channel values of the uncalibrated image by the calculated calibration factor to obtain RGB channel values for a calibrated image.

Figure 5A:
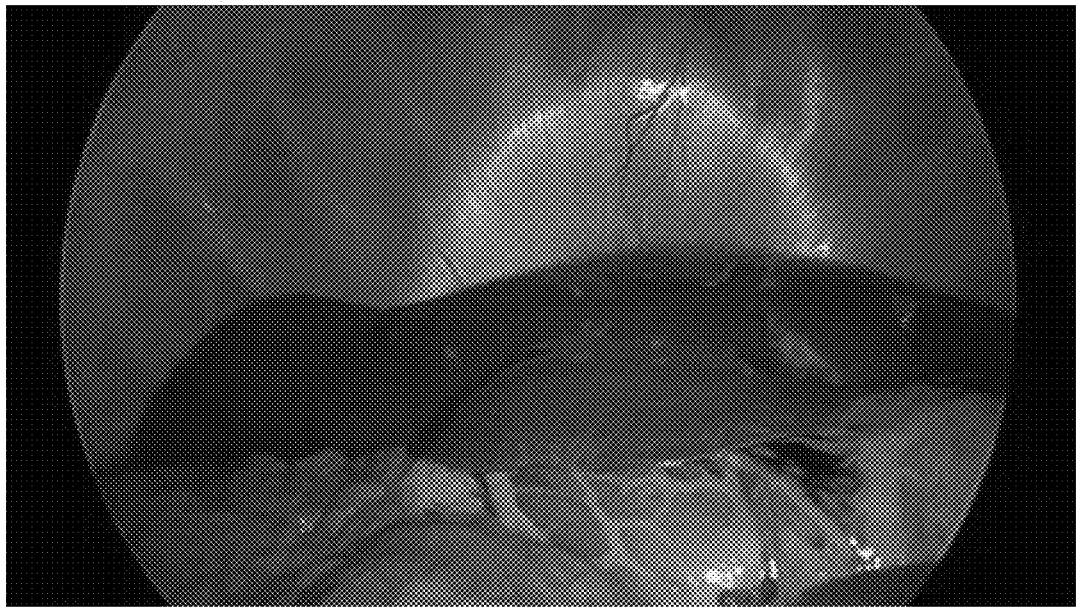
FIGS. 5A-5B show a first example of an anatomical image before and after calibration, in accordance with some embodiments.
Figure 5B:

FIGS. 5A and 5B show a first example of an anatomical image before and after calibration. FIG. 5A shows an uncalibrated image captured by a camera having a brightness setting of level 2. FIG. 5B shows a calibrated image generated based on the image of FIG. 5A, wherein the calibrated image in FIG. 5B was generated by applying the intensity calibration technique described above.

Figure 6A:
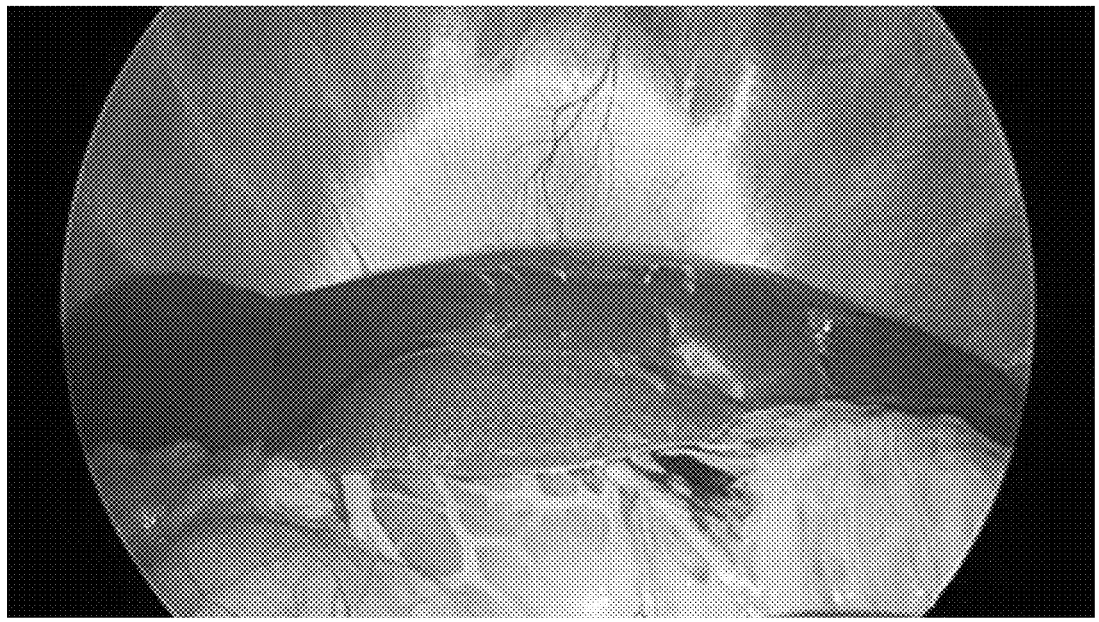
FIGS. 6A-6B show a second example of an anatomical image before and after calibration, in accordance with some embodiments.
Figure 6B:
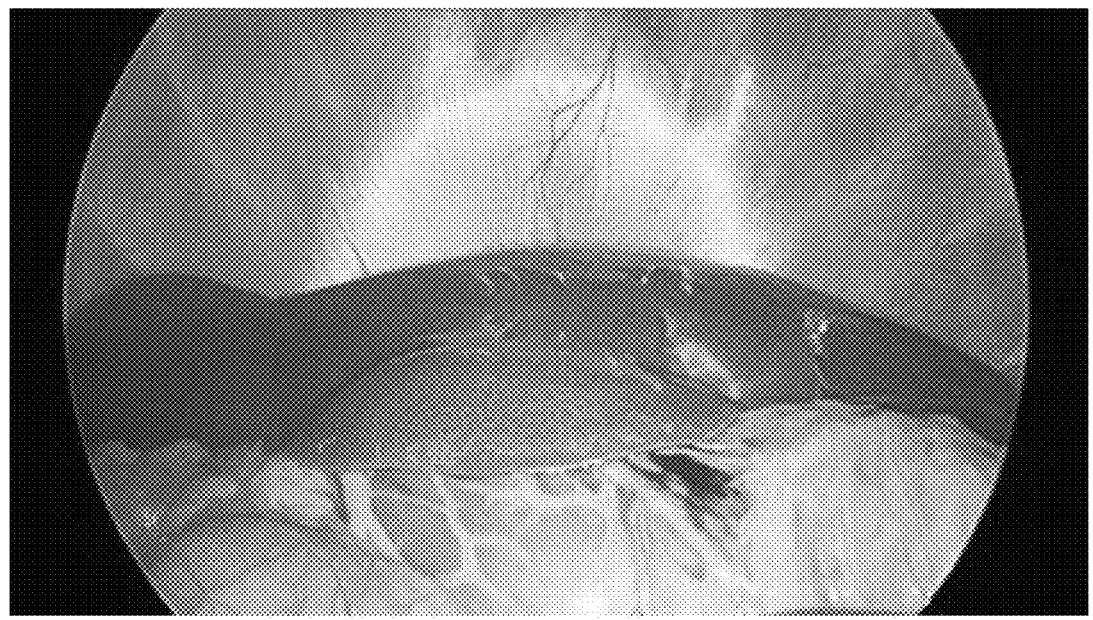

FIGS. 6A and 6B show a second example of an anatomical image before and after calibration. FIG. 6A shows an uncalibrated image captured by a camera having a brightness setting of level 6. FIG. 6B shows a calibrated image generated based on the image of FIG. 6A, wherein the calibrated image in FIG. 6B was generated by applying the intensity calibration technique described above.

As shown, the images in FIGS. 5B and 6B are more visually similar to one another after the calibration process than the images in FIGS. 5A and 6A were to one another before the calibration process.

Figure 7:
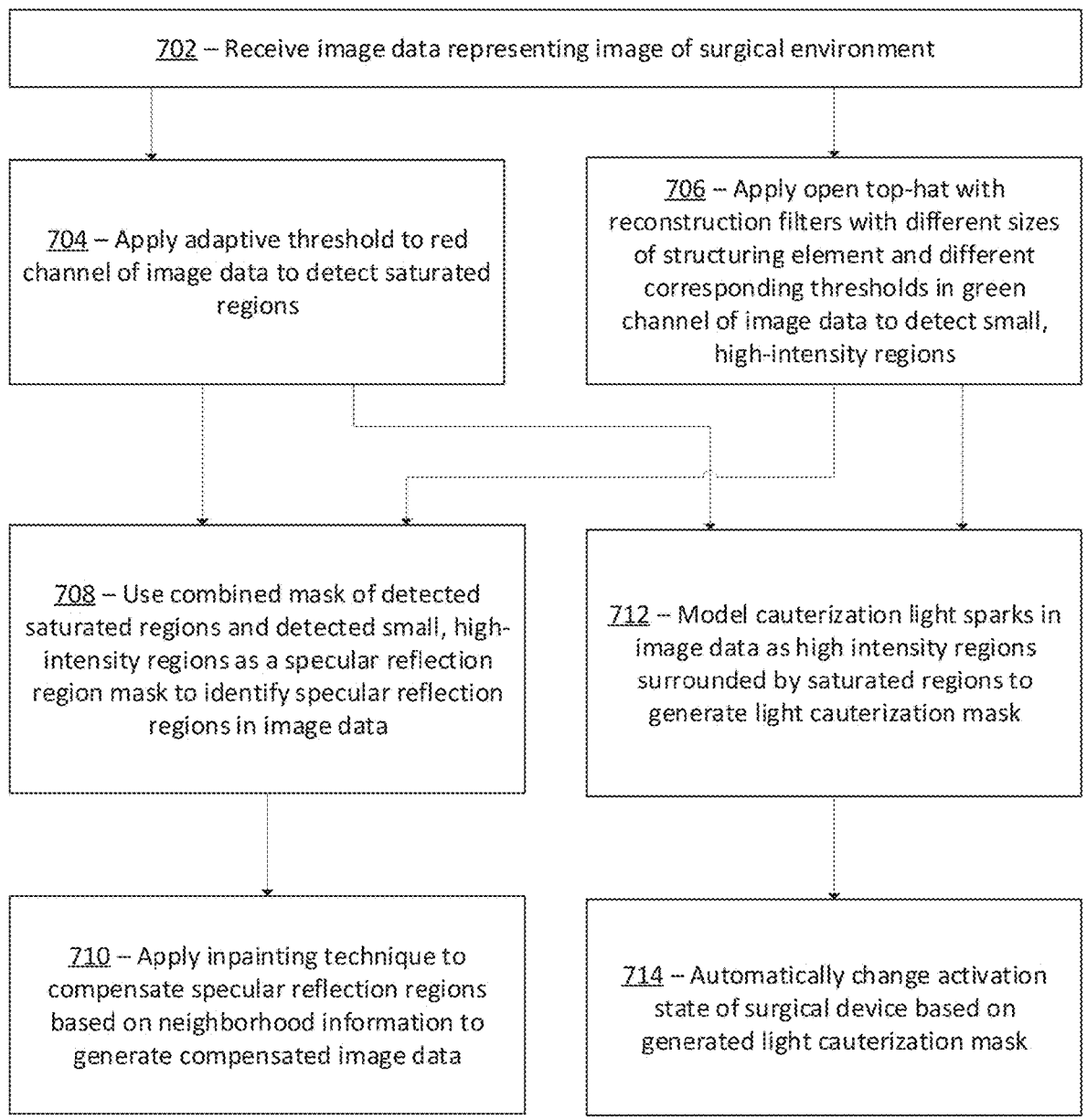
FIG. 7 depicts a flowchart representing an exemplary method for enhancing visualizations and/or managing surgical smoke, in accordance with some embodiments.

FIG. 7 depicts a flowchart representing an exemplary method 700 for managing surgical smoke, in accordance with some embodiments. While the techniques described hereinabove have pertained to managing surgical smoke by assessing smokiness in surgical images (and optionally controlling one or more systems such as a smoke evacuation system in accordance with said assessment), the techniques described with respect to FIG. 7 pertain to alternate or additional methods for managing surgical smoke. In particular, a system may apply a specular reflection algorithm to one or more images (e.g., images or frames from surgical video) in order to automatically detect and recognize images/video of cauterization sparks generated by electro-cauterization during a surgical procedure. Because electro-cauterization may cause surgical smoke, it may be advantageous to, following detection of a cauterization spark, activate a surgical smoke evacuation device or other surgical devices/processes associated with managing surgical smoke.

Use of all or part of method 700 may enable a system to automatically change an activation state of one or more surgical devices based on an assessment generated by a cauterization spark detection algorithm as described herein. In some embodiments, a surgical system may be configured to automatically change an activation state of one or more surgical devices based on both (a) an assessment generated by a cauterization spark detection algorithm as described herein and (b) an assessment generated by a smokiness characterization algorithm such as described hereinabove. In some embodiments, a surgical system may be configured to automatically change an activation state of one or more surgical devices based on an assessment generated by a combined algorithm configured to assess both smokiness and presence/absence of cauterization sparks.

Use of all or part of method 700 may further enable a system to automatically, quickly, and effectively identify an entry point to endoscopic surgical ambience (e.g., the environment inside the body of the patient) with the detection of tissue specular reflection. Specular reflection is commonly a result of light scattering on wet tissue, while other typical surgical room scenes may be less likely to have specular reflection or may have a different pattern of specular reflections.

Use of all or part of method 700 may further enable improved visualization of specular reflection free images and/or video. The quality of visualizations may be enhanced by identifying regions corresponding to specular reflections and applying one or more compensation techniques to said regions, such as applying an image/video inpainting technique.

Below, method 700 sets forth an exemplary method for enhancing visualizations and/or managing surgical smoke including applying an algorithm for detecting/recognizing cauterization sparks in one or more images. As described below in detail, method 700 may enable a surgical smoke management system to receive surgical images or videos, to process the surgical images or videos to detect/recognize a cauterization spark, and to automatically disable or disable one or more surgical smoke management devices based on the determined level of surgical smoke.

In some embodiments, method 700 may be carried out, in whole or in part, by one or more of the components of a system for managing surgical smoke, such as system 100 described above with respect to FIG. 1. In some embodiments, any one or more of the aspects of method 700 may be combined, in whole or in part, with any one or more of the aspects of FIG. 1, and/or with any one or more of the systems, methods, devices, and/or techniques described elsewhere herein.

At block 702, in some embodiments, the system may receive image data representing an image of a surgical environment. In the example of system 100, surgical smoke assessment system 104 may receive image data representing an image of a surgical environment from image data source 102.

The image data received by the system may be in the form of a still image or one or more frames of a video image, and may depict a surgical environment (e.g., an area in and/or near a tissue segment on which surgery is being performed) that may or may not depict a cauterization spark. The image data may be received from an image or video capture device, an image or video broadcasting or relaying device, one or more servers, and/or one or more databases or repositories. The image data received may be received via any suitable form of electronic communication, including wired and/or wireless network communication.

The image data received by the system may comprise a plurality of pixels. One or more of the plurality of pixels constituting the image data may, in some embodiments, be associated with one or more values indicating a brightness (e.g., intensity) for the pixel. In some embodiments, a pixel may be associated with a plurality of values, with each value representing a different color-channel for the pixel. In some embodiments, each pixel may comprise three color-channel values, e.g., one value each for a red, green, and blue color-channel for each pixel.

In some embodiments, the system may perform one or more image pre-processing techniques on the received image data (not shown in FIG. 7). For example, the system may perform cropping, alignment, and/or re-sizing (e.g., scaling) of the received image data before additional processing steps are performed. In some embodiments, the cropping, alignment, and/or re-sizing procedures may share any one or more characteristics in common with the cropping, alignment, and/or re-sizing procedures described above with reference to FIG. 2.

In some embodiments, more than one of the image pre-processing techniques may be performed on the same image data. For example, a single image frame may be subject to any two or more image preprocessing techniques before proceeding to the image processing techniques discussed below. In some embodiments, no image preprocessing techniques may be employed (e.g., the raw image data initially received may be used for the image processing steps described below).

Figure 8:
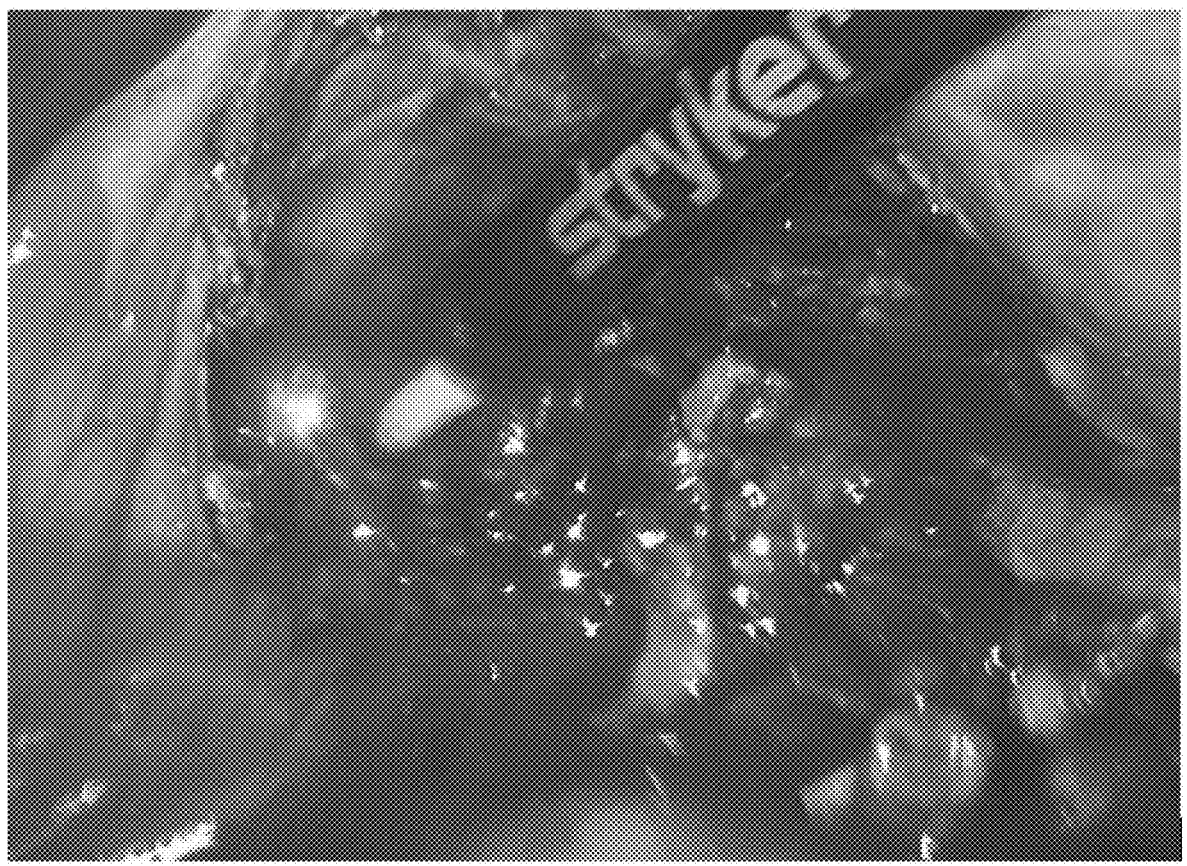
FIG. 8 shows an input image of a laparoscopic procedure, in accordance with some embodiments.

An example of an image received at block 702 in method 700 is shown in FIG. 8. In the example shown, the image is a video frame of a laparoscopic procedure.

At block 704, in some embodiments, the system may apply an adaptive threshold to red channel values of the image data to detect saturated regions. In some embodiments, one or more alternative or additional techniques may be used to identify saturated regions of the image data.

Figure 9A:
FIGS. 9A-9B show a color-saturated region mask, in accordance with some embodiments.
Figure 9B:
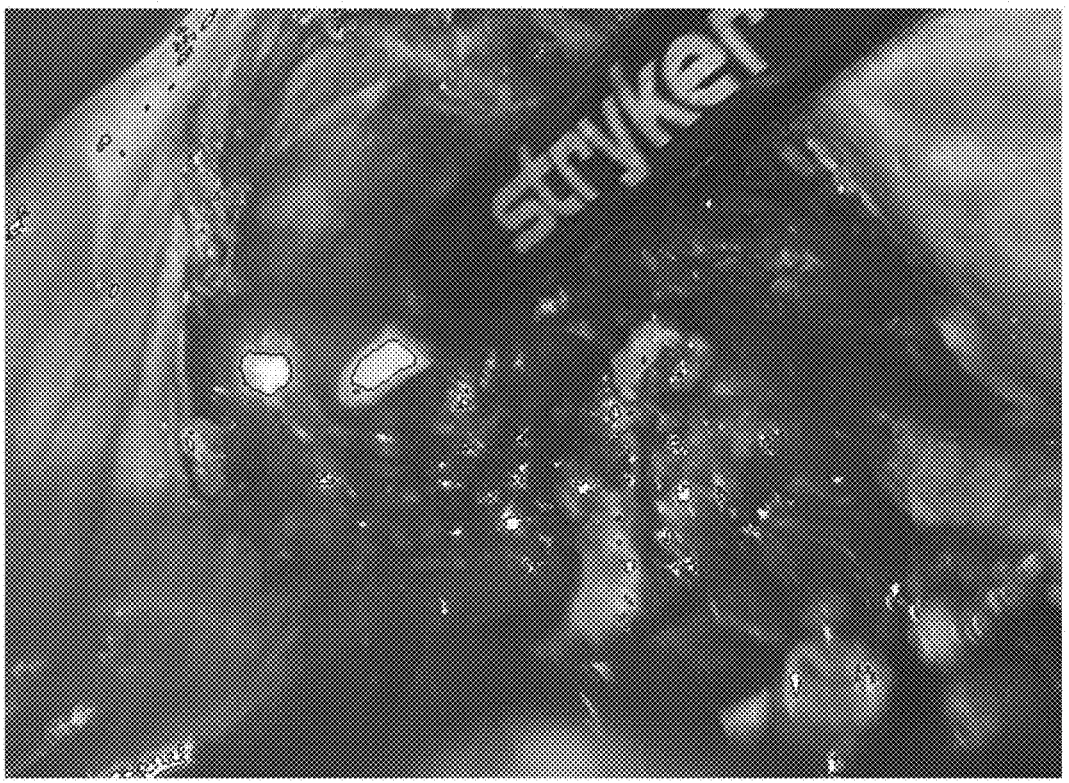

An example of color-saturated region detection in accordance with block 704, based on the image of FIG. 8, is shown in FIGS. 9A-9B. FIG. 9A depicts a color-saturated region mask computed based on the image of FIG. 8; FIG. 9B depicts the color-saturated region mask displayed as an outline overlay on the image of FIG. 8.

At block 706, in some embodiments, the system may apply open top-hat with reconstruction filters with different sizes of structuring element and different corresponding thresholds to green channel values of the image data to detect small, high-intensity regions. In some embodiments, one or more alternative or additional techniques may be used to identify small regions of high-intensity.

Figure 10A:
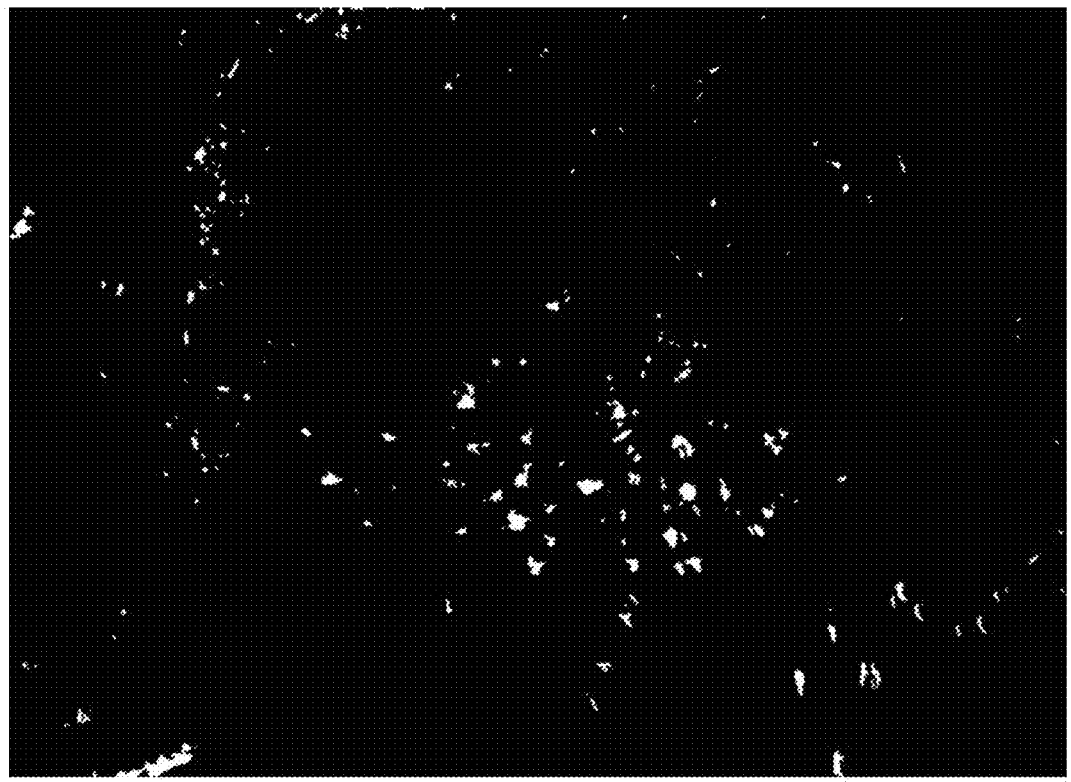
FIGS. 10A-10B show a small, high-intensity region mask, in accordance with some embodiments.
Figure 10B:

An example of small, high-intensity region detection in accordance with block 706, based on the image of FIG. 8, is shown in FIGS. 10A-10B. FIG. 10A depicts a small, high-intensity region mask computed based on the image of FIG. 8; FIG. 10B depicts the small, high-intensity region mask displayed as an outline overlay on the image of FIG. 8.

Blocks 708 and 710, which may follow from blocks 704 and 706, pertain to techniques for enhancing visualizations, for example by generating compensated image data that may compensate for specular reflection regions. The compensated image data that is generated may be stored, analyzed (e.g., using one or more of the image analysis techniques disclosed herein), transmitted, and/or displayed.

At block 708, in some embodiments, the system may use a combined mask of the detected saturated regions and the detected small, high-intensity regions as a specular reflection region mask to identify specular reflection regions in the image data. In some embodiments, regions identified at both block 704 and block 706 may be determined to be regions representing specular reflection in the image data.

Figure 11:
FIG. 11 shows a specular reflection region mask, in accordance with some embodiments.

An example of a specular reflection region mask generated based on the regions identified at blocks 704 and 706 is shown in FIG. 11.

At block 710, in some embodiments, the system may apply one or more inpainting techniques to compensate the identified specular reflection regions based on neighborhood information, thereby generating compensated image data. In some embodiments, one or more alternative or additional techniques may be used to compensate one or more identified specular regions.

Figure 12:
FIG. 12 shows a compensated image of a laparoscopic procedure, in accordance with some embodiments.

An example of a specular-reflection-compensated image associated with compensated image data generated by block 710 is shown in FIG. 12. The image of FIG. 12 is a specular-reflection-compensated image based on the original image of FIG. 8.

Blocks 712 and 714, which may follow from blocks 704 and 706, pertain to techniques for determining whether an image depicts a cauterization spark and for controlling one or more surgical devices based on said determination.

At block 712, in some embodiments, the system may model cauterization light sparks in the image data as high intensity regions surrounded by saturated regions to generate a light cauterization mask. In some embodiments, for a given color-saturated region that has been detected, one or more region properties of the color-saturated region may be analyzed. For example, the system may determine whether the color saturated region contains an identified local high-intensity region; the system may determine a ratio of red intensity to green intensity of the color saturated region; the system may determine an area of the color saturated region; and/or the system may determine an eccentricity of the color-saturated region. One or more region properties of the color-saturated region may be compared to a set of one or more predefined (and/or user specified and/or dynamically determined) criteria to determine whether the region properties satisfies the set of one or more predefined criteria. The system may determine that color-saturated regions satisfying the set of criteria correspond to cauterization sparks, and the system may generate the light cauterization mask based on said determination indicating that those regions correspond to cauterization sparks.

In some embodiments, in addition to or alternatively to assessing color-saturated regions to determine whether they correspond to cauterization sparks, the system may assess small, high-intensity regions identified (e.g., as at block 706) to determine whether they correspond to cauterization sparks.

Figure 13A:
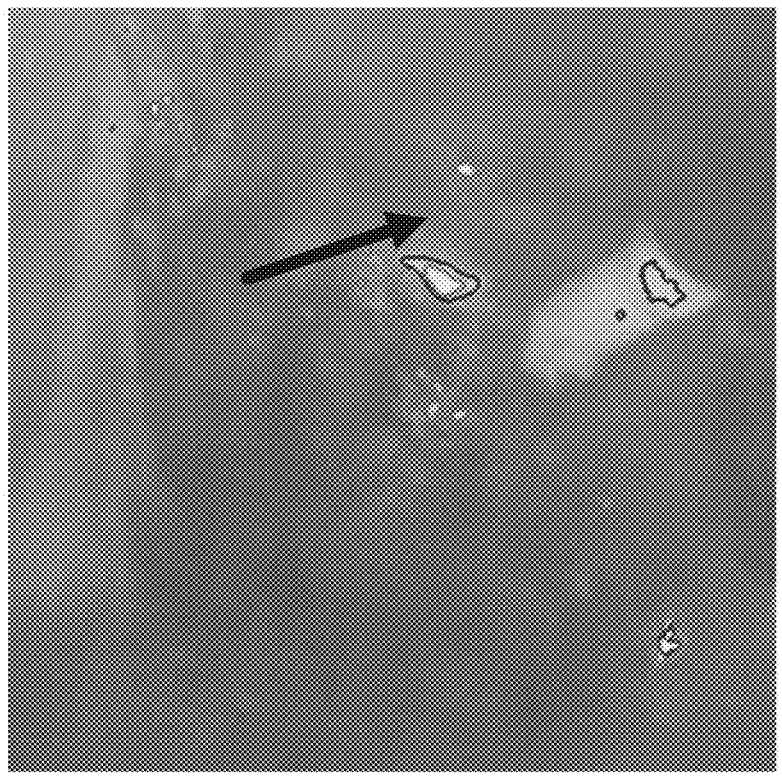
FIGS. 13A-13B show calculation and display of a light cauterization mask, in accordance with some embodiments.
Figure 13B:
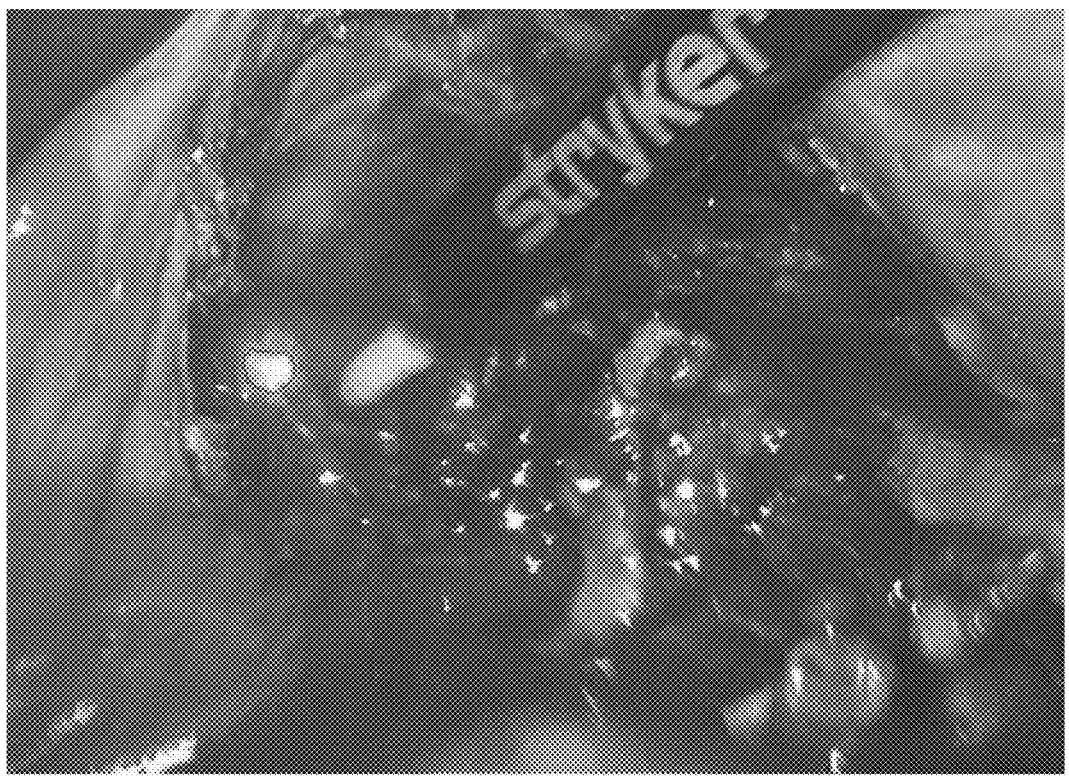

An example of cauterization spark identification in accordance with block 712 is shown in the images of FIGS. 13A-13B. FIG. 13A depicts a region of an image with outline overlays from the images of both a color-saturated region mask displayed as an outline overlay and a small, high-intensity region mask displayed as an outline overlay. As highlighted by the arrow, the image contains one region showing a small, high intensity region contour surrounded by saturated region contour. The system may recognize this region as a region corresponding to a cauterization spark. FIG. 13B shows a light cauterization mask generated, e.g., based on underlying image data such as based on the image from FIG. 8, wherein the region corresponding to the saturated region contour with a small, high-intensity region contour contained therein is depicted as an outline representing the light cauterization mask overlaid on the original image.

At block 714, in some embodiments, the system may automatically change an activation state of one or more surgical devices based on the generated light cauterization mask. In some embodiments, the system may determine whether to change an activation state based on whether or not the generated light cauterization mask indicates that a cauterization spark (e.g., at least one cauterization spark) is depicted in the original image data (e.g., whether a spark is detected in a frame and/or in one or more frames of an analyzed series of frames). In some embodiments, automatically changing an activation state at block 714 may share any one or more characteristics in common with automatically changing an activation state at block 240 as discussed above.

Figure 14:
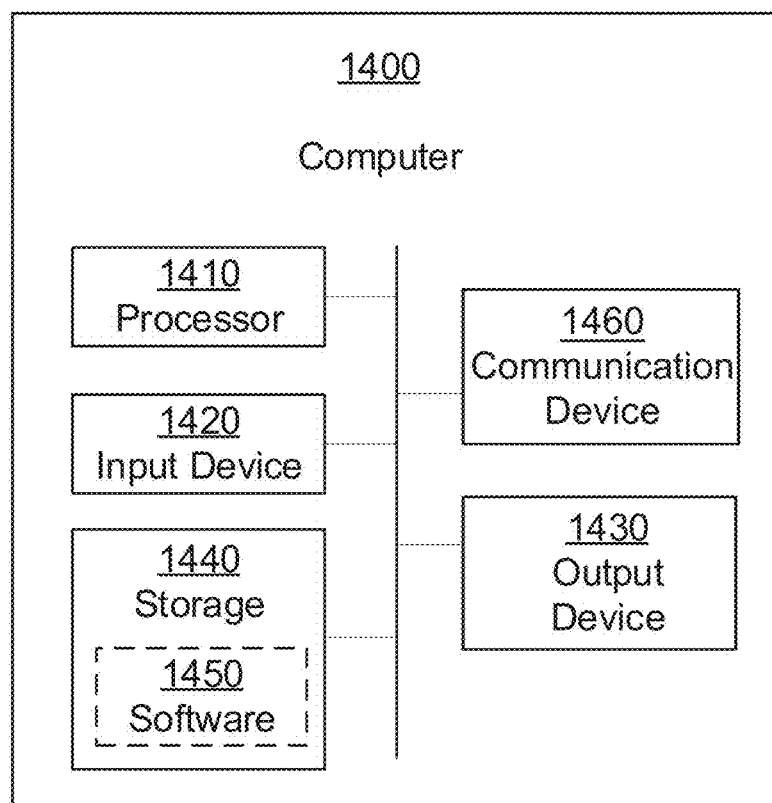
FIG. 14 depicts a computer, in accordance with some embodiments.

FIG. 14 illustrates a computer, in accordance with some embodiments. Computer 1400 can be a component of a system for managing surgical smoke, such as system 100 and/or any of its subcomponents described above with respect to FIG. 1. In some embodiments, computer 1400 may be configured to execute a method for managing surgical smoke, such as all or part of method 200 described above with respect to FIGS. 2A-2B and/or method 700 described above with respect to FIG. 7. In some embodiments, additionally or alternatively, computer 1400 may be configured to execute a method for image calibration, such as all or part of the techniques described above with respect to FIGS. 5A-5B and 6A-6B. In some embodiments, additionally or alternatively, computer 1400 may be configured to execute a method for enhancement of a visualization of an image, such as all or part of method 700 described above with respect to FIG. 7.

Computer 1400 can be a host computer connected to a network. Computer 1400 can be a client computer or a server. As shown in FIG. 14, computer 1400 can be any suitable type of microprocessor-based device, such as a personal computer; workstation; server; or handheld computing device, such as a phone or tablet. The computer can include, for example, one or more of processor 310, input device 1420, output device 1430, storage 1440, and communication device 1460.

Input device 1420 can be any suitable device that provides input, such as a touch screen or monitor, keyboard, mouse, or voice-recognition device. Output device 1430 can be any suitable device that provides output, such as a touch screen, monitor, printer, disk drive, or speaker.

Storage 1440 can be any suitable device that provides storage, such as an electrical, magnetic, or optical memory, including a RAM, cache, hard drive, CD-ROM drive, tape drive, or removable storage disk. Communication device 1460 can include any suitable device capable of transmitting and receiving signals over a network, such as a network interface chip or card. The components of the computer can be connected in any suitable manner, such as via a physical bus or wirelessly. Storage 1440 can be a non-transitory computer-readable storage medium comprising one or more programs, which, when executed by one or more processors, such as processor 1410, cause the one or more processors to execute methods described herein, such as all or part of method 200 described above with respect to FIGS. 2A-2B and/or all or part of method 700 described above with respect to FIG. 7.

Software 1450, which can be stored in storage 1440 and executed by processor 1410, can include, for example, the programming that embodies the functionality of the present disclosure (e.g., as embodied in the systems, computers, servers, and/or devices as described above). In some embodiments, software 1450 can be implemented and executed on a combination of servers such as application servers and database servers.

Software 1450 can also be stored and/or transported within any computer-readable storage medium for use by or in connection with an instruction execution system, apparatus, or device, such as those described above, that can fetch and execute instructions associated with the software from the instruction execution system, apparatus, or device. In the context of this disclosure, a computer-readable storage medium can be any medium, such as storage 1440, that can contain or store programming for use by or in connection with an instruction execution system, apparatus, or device.

Software 1450 can also be propagated within any transport medium for use by or in connection with an instruction execution system, apparatus, or device, such as those described above, that can fetch and execute instructions associated with the software from the instruction execution system, apparatus, or device. In the context of this disclosure, a transport medium can be any medium that can communicate, propagate, or transport programming for use by or in connection with an instruction execution system, apparatus, or device. The transport-readable medium can include, but is not limited to, an electronic, magnetic, optical, electromagnetic, or infrared wired or wireless propagation medium.

Computer 1400 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computer 1400 can implement any operating system suitable for operating on the network. Software 1450 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

What is claimed is:

1. A surgical system, the system comprising:
one or more processors configured to:
receive image data representing an image of a surgical environment;
generate, based on the received image data, a set of one or more values representing atmospheric light of the image data;
generate, based on the received image data, a set of one or more representative contrast values;
determine, based on the one or more values representing atmospheric light and based on the one or more representative contrast values, whether the received image data satisfies one or more surgical smoke conditions,
wherein determining whether the received image data satisfies one or more surgical smoke conditions comprises calculating a smoke degree score based on the set of one or more values representing atmospheric light of the image data and based on the set of one or more representative contrast values,
wherein calculating the smoke degree score comprises performing one or more linear regressions based on the set of one or more values representing atmospheric light of the image data and based on the set of one or more representative contrast values.

2. The system of claim 1, wherein:
the set of one or more values representing atmospheric light of the image data is generated by the system based on a set of one or more values representing a bright channel of the image data; and
the set of one or more values representing the bright channel is generated by the system based on the image data.

3. The system of claim 2, wherein generating the set of one or more values representing the bright channel of the image data comprises:
for each pixel of the image data, selecting, as a respective bright channel pixel value, a maximum color-channel value from among a group of pixels of the image data within a respective patch including the respective pixel.

4. The system of claim 2, wherein generating the set of one or more values representing atmospheric light comprises:
 calculating a first term comprising a set of one or more maximum values of the one or more values representing the bright channel;
 calculating a second term comprising a set of one or more representative bright-channel values based on the one or more values representing the bright channel;
 calculating a sum of the first term and the second term to generate the set of one or more values representing atmospheric light.

5. The system of claim 4, wherein calculating the first term comprises generating a one-dimensional matrix based on the one or more values representing the bright channel.

6. The system of claim 4, wherein calculating the second term comprises generating a one-dimensional matrix based on the one or more values representing the bright channel.

7. The system of claim 4, wherein the first term is weighted by a constant $c_1$.

8. The system of claim 7, wherein the second term is weighted by a second constant equal to $(1-c_1)$.

9. The system of claim 2, wherein:
 the set of one or more representative contrast values is generated by the system based on the one or more values representing the bright channel of the image data and based on one or more values representing a dark channel of the image data; and
 the set of one or more values representing the dark channel is generated by the system based on the image data.

10. The system of claim 9, wherein generating the set of one or more values representing the dark channel of the image data comprises:
 for each pixel of the image data, selecting, as a respective dark channel pixel value, a minimum color-channel value from among a group of pixels of the image data within a respective patch including the respective pixel.

11. The system of claim 9, wherein generating the set of one or more representative contrast values comprises:
 calculating a third term comprising a set of one or more representative bright-channel values based on the one or more values representing the bright channel;
 calculating a fourth term comprising a set of one or more representative dark-channel values based on the one or more values representing the dark channel;
 calculating a set of one or more difference values based on a difference between the fourth term and the third term to generate the set of one or more representative contrast values.

12. The system of claim 1, wherein calculating the smoke degree score comprises calculating an exponential value based on one or more slopes of the one or more linear regressions.

13. The system of claim 12, wherein the exponential value is calculated based on an exponent comprising a term based on a sum of two or more of the slope values.

14. The system of claim 1, wherein determining whether the received image data satisfies one or more surgical smoke conditions comprises comparing the smoke degree score to a first threshold value.

15. The system of claim 1, wherein determining whether the received image data satisfies one or more surgical smoke conditions comprises calculating an adjusted set of one or more atmospheric light values.

16. The system of claim 15, wherein determining whether the received image data satisfies one or more surgical smoke conditions comprises:
 comparing the adjusted set of one or more values representing atmospheric light of the image data to a second threshold value; and
 comparing the set of one or more representative contrast values to a third threshold value.

17. The system of claim 1, further comprising a surgical device configured to automatically change between activation states, wherein the processor is further configured to:
 based on the determination of whether the received image data satisfies the one or more surgical smoke conditions, automatically change an activation state of the surgical device.

18. The system of claim 17, wherein changing the activation state of the surgical device comprises performing an operation selected from turning the device on and turning the device off.

19. The system of claim 17, wherein the surgical device comprises a smoke evacuation system.

20. The system of claim 17, wherein the surgical device comprises an image processing system.

21. The system of claim 1, wherein the image data representing the image of a surgical environment is a region extracted from an image larger than the region.

22. The system of claim 1, wherein the one or more processors are configured to perform a scaling operation on the image data.

23. A method, performed at a surgical system, the method comprising:
 receiving image data representing an image of a surgical environment;
 generating, based on the received image data, a set of one or more values representing atmospheric light of the image data;
 generating, based on the received image data, a set of one or more representative contrast values;
 determining, based on the one or more values representing atmospheric light and based on the one or more representative contrast values, whether the received image data satisfies one or more surgical smoke conditions,
 wherein determining whether the received image data satisfies one or more surgical smoke conditions comprises calculating a smoke degree score based on the set of one or more values representing atmospheric light of the image data and based on the set of one or more representative contrast values,
 wherein calculating the smoke degree score comprises performing one or more linear regressions based on the set of one or more values representing atmospheric light of the image data and based on the set of one or more representative contrast values.

24. A non-transitory computer-readable storage medium storing instructions configured to be executed by a surgical system and to cause the surgical system to:
 receive image data representing an image of a surgical environment;
 generate, based on the received image data, a set of one or more values representing atmospheric light of the image data;
 generate, based on the received image data, a set of one or more representative contrast values;
 determine, based on the one or more values representing atmospheric light and based on the one or more representative contrast values, whether the received image data satisfies one or more surgical smoke conditions,
wherein determining whether the received image data satisfies one or more surgical smoke conditions comprises calculating a smoke degree score based on the set of one or more values representing atmospheric light of the image data and based on the set of one or more representative contrast values,
wherein calculating the smoke degree score comprises performing one or more linear regressions based on the set of one or more values representing atmospheric light of the image data and based on the set of one or more representative contrast values.

25. A surgical system, the system comprising:
one or more processors configured to:
receive image data representing an image of a surgical environment;
detect, based on the received image data, one or more saturated regions in the image;
detect, based on the received image data, one or more high-intensity regions in the image data;
generate, based on the one or more saturated regions and on the one or more high-intensity regions, data representing cauterization light sparks in the image.

26. The system of claim 25, wherein detecting the one or more saturated regions in the image data is based on red channel data of the image data.

27. The system of claim 25, wherein detecting the one or more saturated regions in the image data comprises applying an adaptive threshold to the image data.

28. The system of claim 25, wherein detecting the one or more high-intensity regions in the image data is based on green channel data of the image data.

29. The system of claim 25, wherein detecting the one or more high-intensity regions in the image data comprises applying open top-hat with reconstruction filters to the image data.

30. The system of claim 29, wherein the reconstruction filters comprise different sizes of structuring elements and different corresponding thresholds.

31. The system of claim 25, wherein generating the data representing cauterization light sparks in the image comprises modeling cauterization light sparks in the image data as one or more of the high-intensity regions surrounded by one or more of the saturated regions.

32. The system of claim 25, wherein the data representing cauterization light sparks in the image comprises a mask.

33. The system of claim 25, further comprising a surgical device configured to automatically change between activation states, wherein the processor is further configured to:
based on the data representing cauterization light sparks in the image, automatically determine whether to change an activation state of the surgical device.

34. The system of claim 33, wherein automatically determining whether to change the activation state of the surgical device comprises comparing the data representing cauterization light sparks to one or more threshold values.

35. The system of claim 33, wherein changing the activation state of the surgical device comprises performing an operation selected from turning the device on and turning the device off.

36. The system of claim 33, wherein the surgical device comprises a smoke evacuation system.

37. The system of claim 33, wherein the surgical device comprises an image processing system.

38. The system of claim 25, wherein the image data representing the image of a surgical environment is a region extracted from an image larger than the region.

39. The system of claim 25, wherein the one or more processors are configured to perform a scaling operation on the image data.

40. The system of claim 25, wherein the one or more processors configured to generate, based on the one or more saturated regions and on the one or more high-intensity regions, data representing one or more specular reflection regions in the image.

41. The system of claim 40, wherein generating the data representing one or more specular reflection regions comprises generating a combined mask based on the one or more saturated regions and on the one or more high-intensity regions.

42. The system of claim 40, wherein the one or more processors are configured to generate modified image data by compensating the one or more specular reflection regions.

43. The system of claim 42, wherein compensating the one or more specular reflection regions comprises applying one or more inpainting techniques to compensate the one or more specular reflection regions based on neighborhood information.

44. A method, performed at a surgical system, the method comprising:
receiving image data representing an image of a surgical environment;
detecting, based on the received image data, one or more saturated regions in the image;
detecting, based on the received image data, one or more high-intensity regions in the image data;
generating, based on the one or more saturated regions and on the one or more high-intensity regions, data representing cauterization light sparks in the image.

45. A non-transitory computer-readable storage medium storing instructions configured to be executed by a surgical system and to cause the surgical system to:
receive image data representing an image of a surgical environment;
detect, based on the received image data, one or more saturated regions in the image;
detect, based on the received image data, one or more high-intensity regions in the image data;
generate, based on the one or more saturated regions and on the one or more high-intensity regions, data representing cauterization light sparks in the image.

46. A surgical system, the system comprising:
one or more processors configured to:
receive image data representing an image of a surgical environment;
generate, based on the received image data, a set of one or more values representing atmospheric light of the image data;
generate, based on the received image data, a set of one or more representative contrast values;
determine, based on the one or more values representing atmospheric light and based on the one or more representative contrast values, whether the received image data satisfies one or more surgical smoke conditions;
detect, based on the received image data, one or more saturated regions in the image;
detect, based on the received image data, one or more high-intensity regions in the image data; and generate, based on the one or more saturated regions and on the one or more high-intensity regions, data representing cauterization light sparks in the image.

47. The system of claim 46, further comprising a surgical device configured to automatically change between activation states, wherein the processor is further configured to:
based on the determination of whether the received image data satisfies the one or more surgical smoke conditions and based on the data representing cauterization light sparks in the image, automatically determine whether to change an activation state of the surgical device.

48. A method, performed at a surgical system, the method comprising:
receiving image data representing an image of a surgical environment;
generating, based on the received image data, a set of one or more values representing atmospheric light of the image data;
generating, based on the received image data, a set of one or more representative contrast values;
determining, based on the one or more values representing atmospheric light and based on the one or more representative contrast values, whether the received image data satisfies one or more surgical smoke conditions;
detecting, based on the received image data, one or more saturated regions in the image;
detecting, based on the received image data, one or more high-intensity regions in the image data;
generating, based on the one or more saturated regions and on the one or more high-intensity regions, data representing cauterization light sparks in the image.

49. A non-transitory computer-readable storage medium storing instructions configured to be executed by a surgical system and to cause the surgical system to:
receive image data representing an image of a surgical environment;
generate, based on the received image data, a set of one or more values representing atmospheric light of the image data;
generate, based on the received image data, a set of one or more representative contrast values;
determine, based on the one or more values representing atmospheric light and based on the one or more representative contrast values, whether the received image data satisfies one or more surgical smoke conditions;
detect, based on the received image data, one or more saturated regions in the image;
detect, based on the received image data, one or more high-intensity regions in the image data;
generate, based on the one or more saturated regions and on the one or more high-intensity regions, data representing cauterization light sparks in the image.

* * * * *